(12) United States Patent
Nikolavsky et al.

(10) Patent No.: US 11,559,297 B2
(45) Date of Patent: Jan. 24, 2023

(54) SUTURING DEVICE AND METHODS OF USE THEREOF

(71) Applicant: THE RESEARCH FOUNDATION FOR THE STATE UNIVERSITY OF NEW YORK, Syracuse, NY (US)

(72) Inventors: Dmitriy Nikolavsky, Jamesville, NY (US); Gennady Bratslavsky, Fayetteville, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 275 days.

(21) Appl. No.: 16/604,858

(22) PCT Filed: Apr. 13, 2018

(86) PCT No.: PCT/US2018/027563
§ 371 (c)(1),
(2) Date: Oct. 11, 2019

(87) PCT Pub. No.: WO2018/191661
PCT Pub. Date: Oct. 18, 2018

(65) Prior Publication Data
US 2020/0069306 A1 Mar. 5, 2020

Related U.S. Application Data

(60) Provisional application No. 62/500,633, filed on May 3, 2017, provisional application No. 62/485,615, filed on Apr. 14, 2017.

(51) Int. Cl.
*A61B 17/04* (2006.01)
*A61B 17/06* (2006.01)

(52) U.S. Cl.
CPC ...... *A61B 17/0469* (2013.01); *A61B 17/0491* (2013.01); *A61B 17/06109* (2013.01);
(Continued)

(58) Field of Classification Search
CPC ............ A61B 17/0469; A61B 17/0491; A61B 17/06166
See application file for complete search history.

(56) References Cited

U.S. PATENT DOCUMENTS 3,840,017 A 10/1974 Violante
4,224,947 A 9/1980 Fukuda
(Continued)

FOREIGN PATENT DOCUMENTS

WO 2000/067643 A1 11/2000
WO 2003063712 A1 8/2003
WO 2012011791 A2 1/2012

OTHER PUBLICATIONS

International Search Report and Written Opinion for corresponding Application No. PCT/US2018/027563 (dated Jul. 3, 2018).

*Primary Examiner* — Tuan V Nguyen
(74) *Attorney, Agent, or Firm* — Lance D. Reich; Peter Fallon; Austin Winter

(57) ABSTRACT

A suturing device includes a hollow needle. The hollow needle has a length extending between a proximal end and a distal end and defining a lumen having an inner diameter. The suturing device further includes a length of surgical suture having a leading end and a trailing end and an outer diameter smaller than the inner diameter of the lumen. At least a portion of the surgical suture is located within the lumen of the hollow needle. A surgical kit including the suturing device and methods of using the suturing device of the present invention are also disclosed.

20 Claims, 14 Drawing Sheets

(52) U.S. Cl.
CPC ... *A61B 17/06166* (2013.01); *A61B 17/06114* (2013.01); *A61B 2017/061* (2013.01); *A61B 2017/06171* (2013.01); *A61B 2017/06176* (2013.01)

(56) References Cited

U.S. PATENT DOCUMENTS

| | | | |
|---|---|---|---|
| 6,221,085 B1 * | 4/2001 | Djurovic | A61B 17/0469 |
| | | | 606/144 |
| 7,226,468 B2 * | 6/2007 | Ruff | A61B 17/06109 |
| | | | 606/213 |
| 7,842,046 B1 | 11/2010 | Nakao | |
| 2005/0283171 A1 * | 12/2005 | Bellafiore | A61B 17/06109 |
| | | | 606/144 |
| 2006/0149280 A1 | 7/2006 | Harvie et al. | |
| 2010/0042117 A1 | 2/2010 | Kim et al. | |
| 2010/0318105 A1 | 12/2010 | Jayant | |
| 2011/0202074 A1 | 8/2011 | Talmo et al. | |
| 2012/0209254 A1 | 8/2012 | Park et al. | |
| 2015/0142019 A1 * | 5/2015 | Sakai | A61B 17/0482 |
| | | | 606/146 |
| 2017/0252035 A1 * | 9/2017 | Miraki | A61B 17/06 |

* cited by examiner

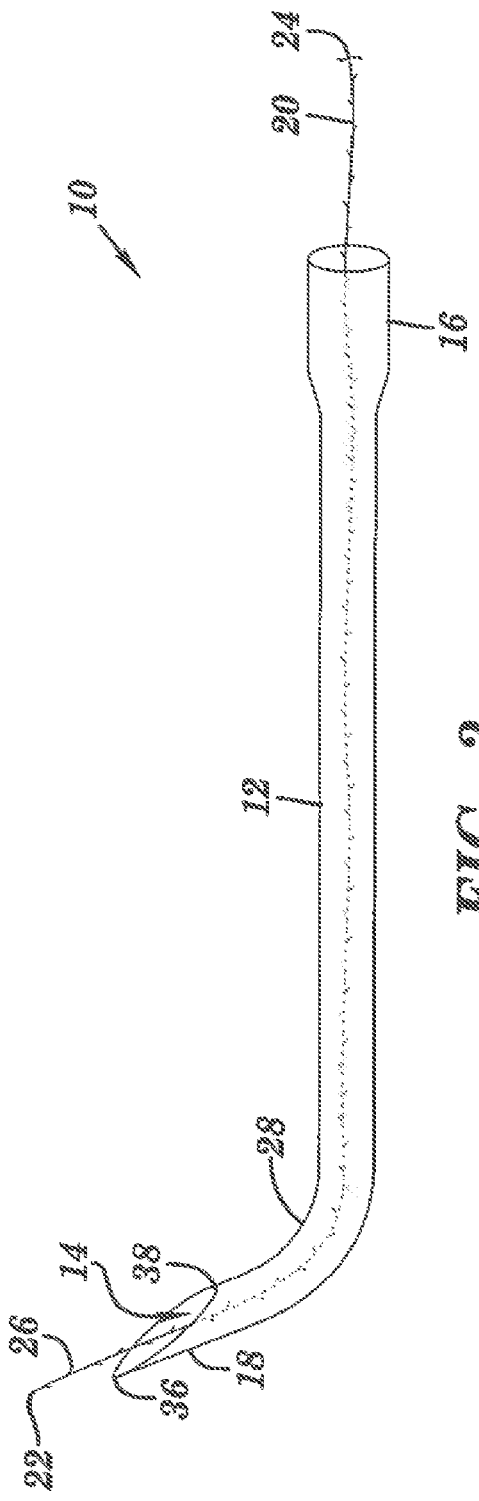
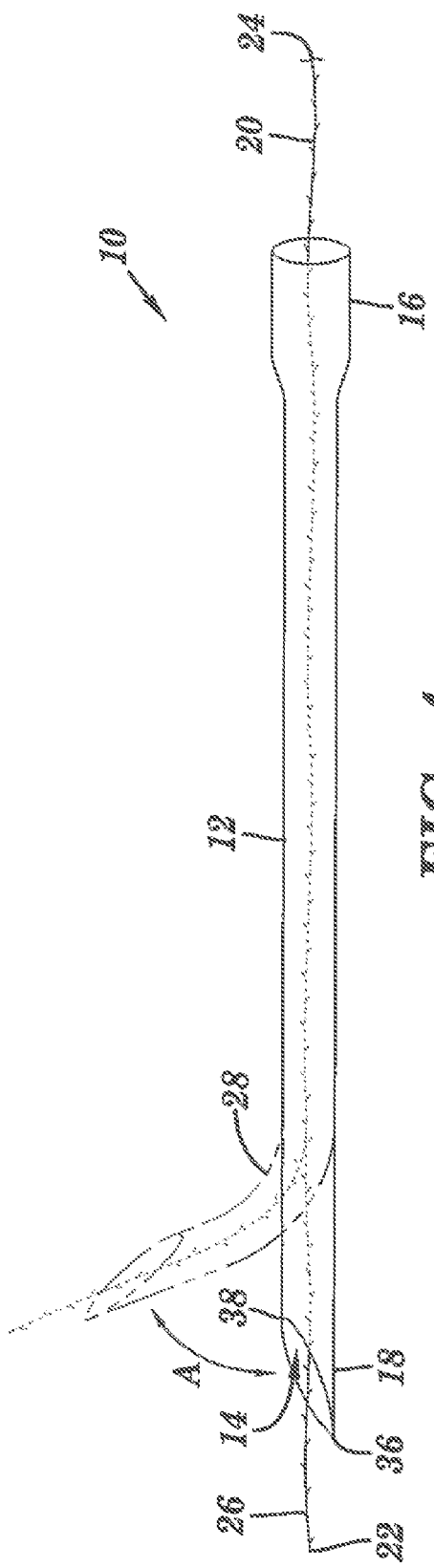

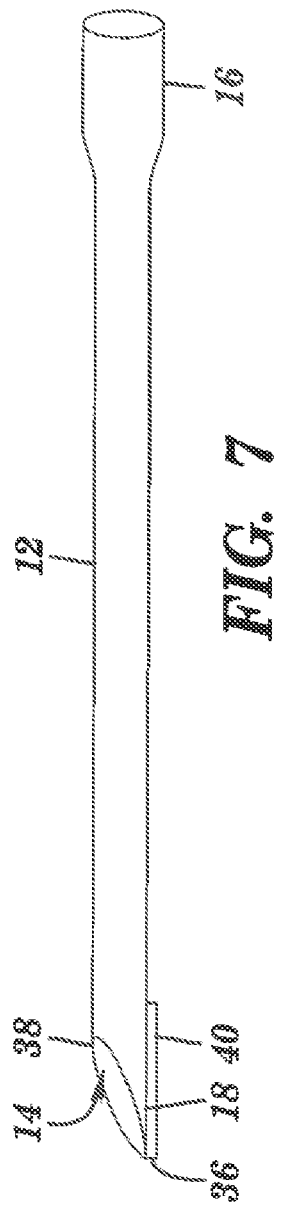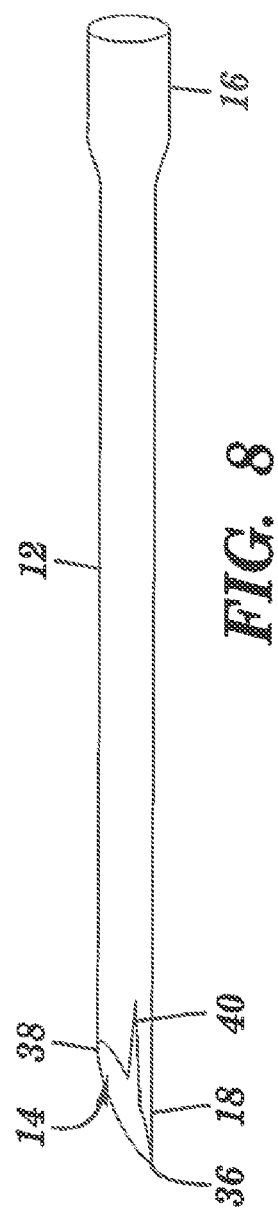

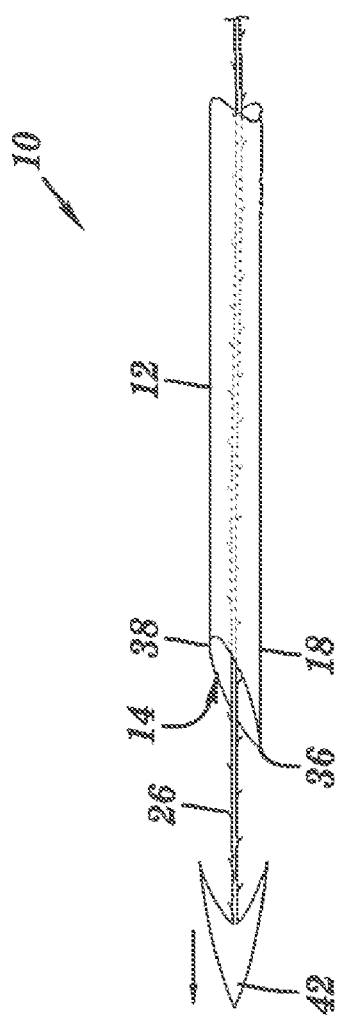
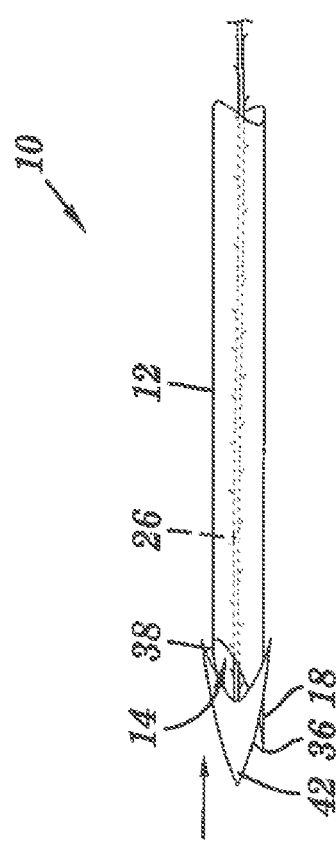

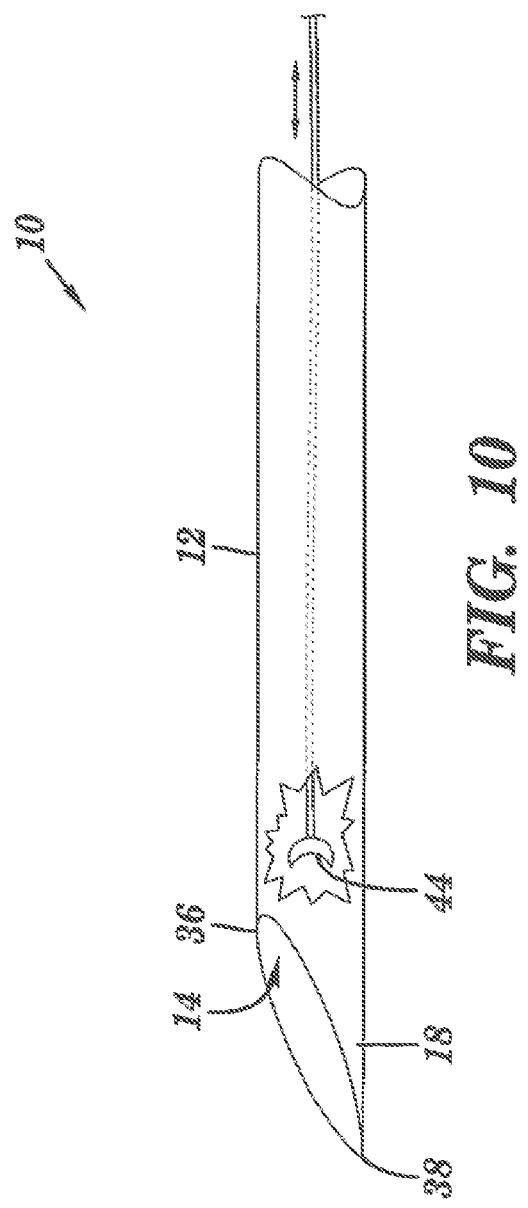

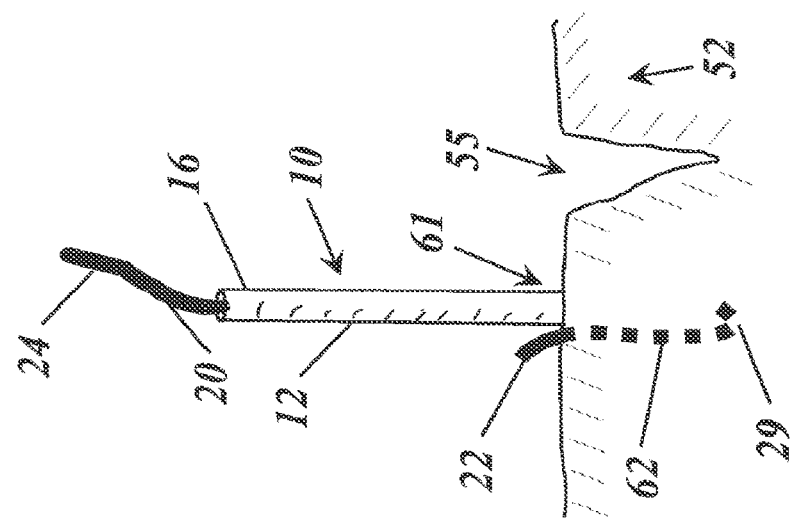
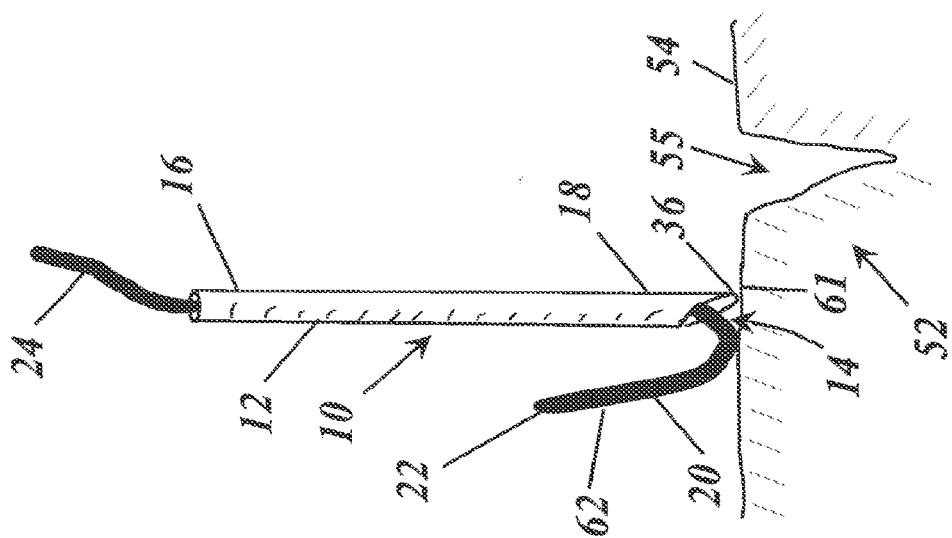

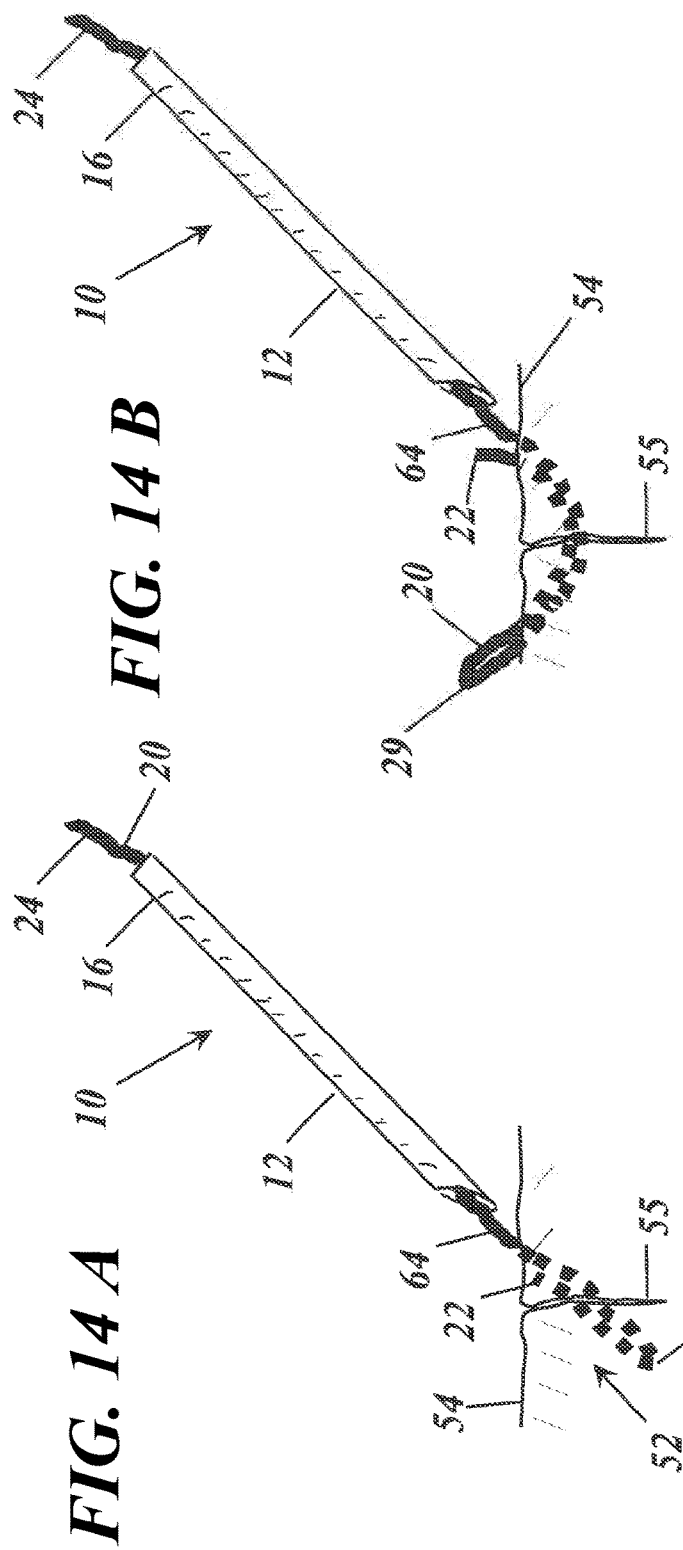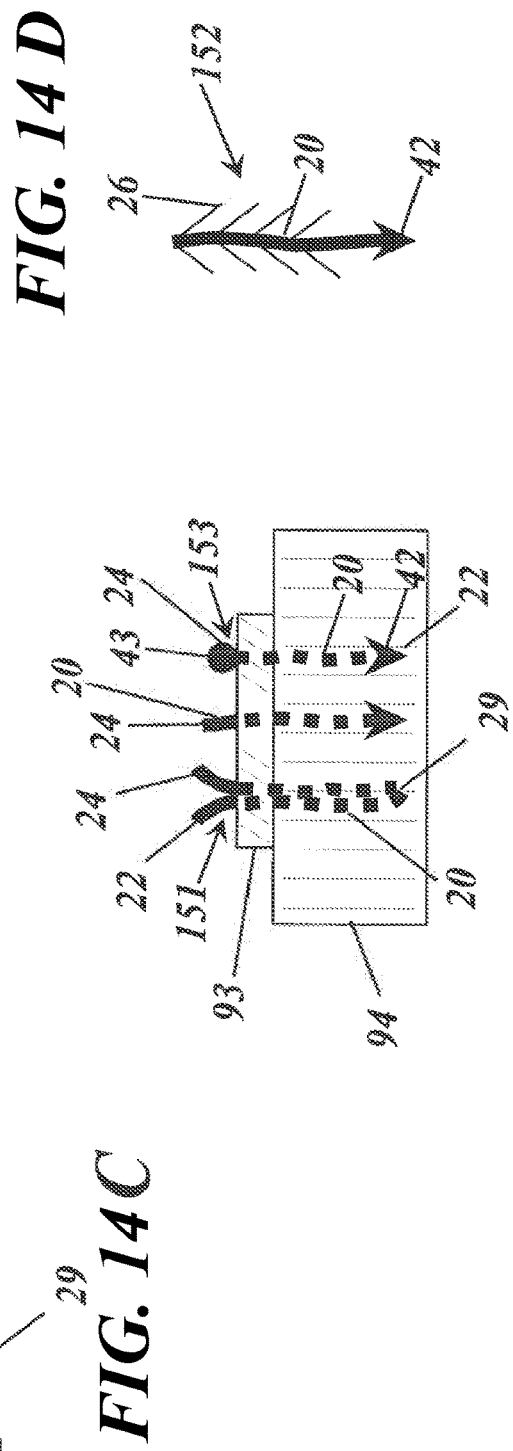

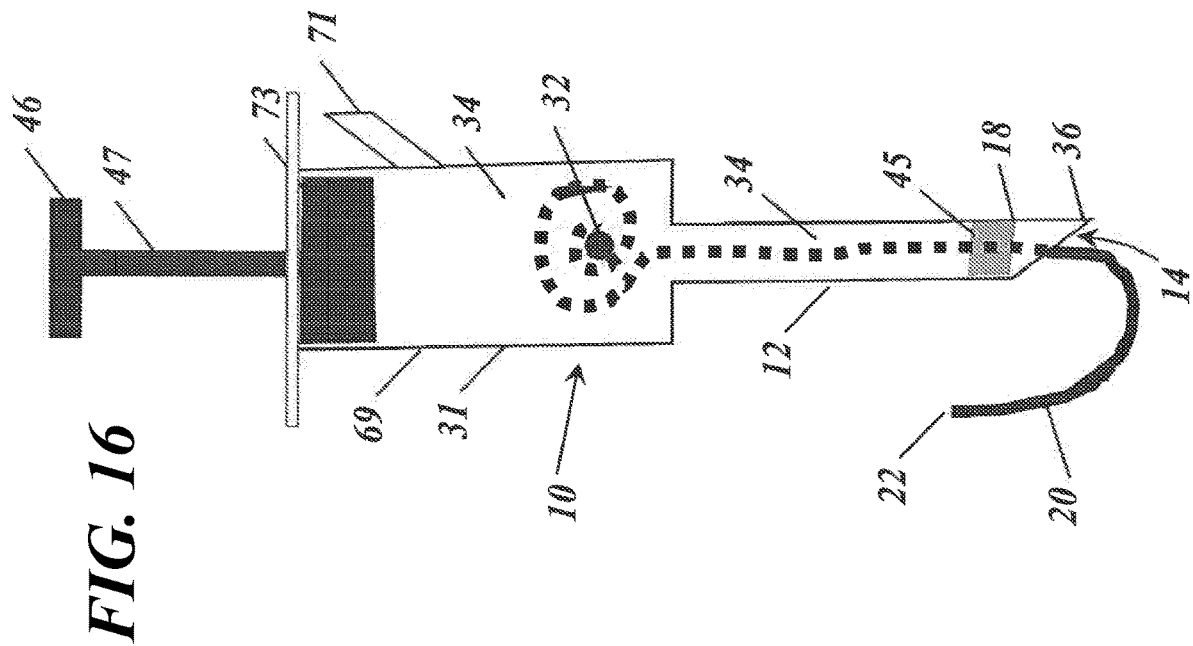

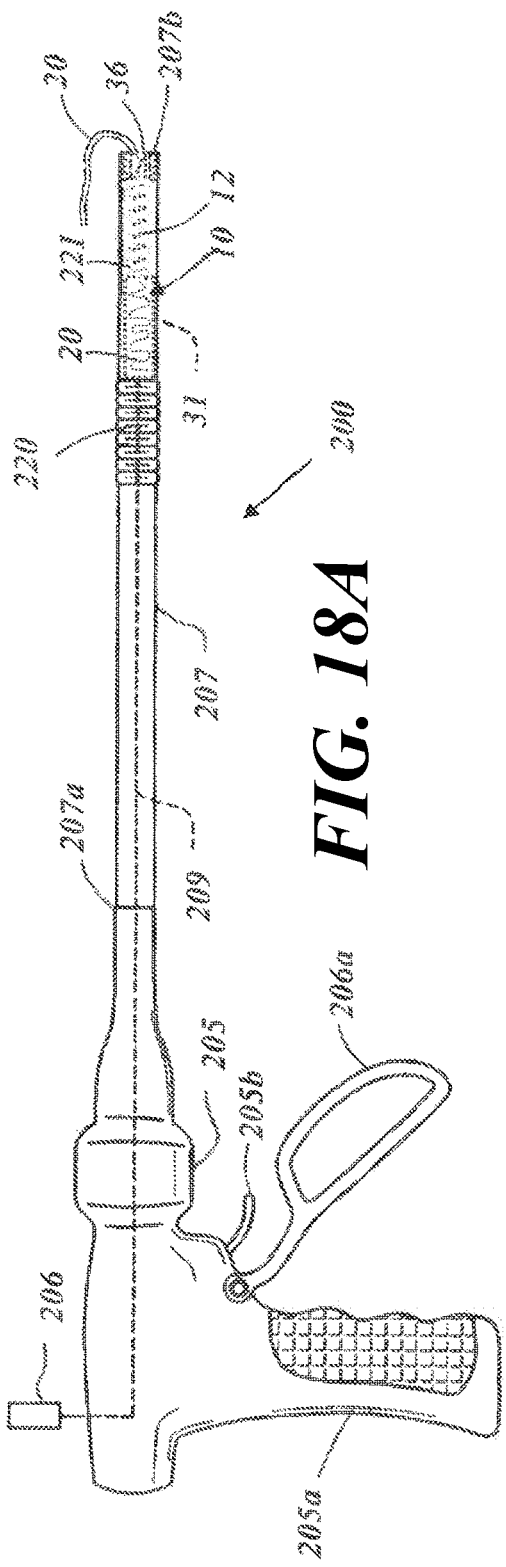
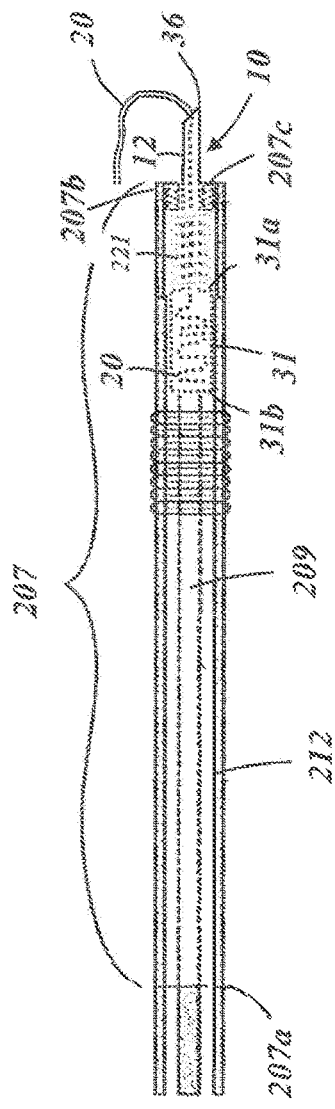

SUTURING DEVICE AND METHODS OF USE THEREOF

CROSS-REFERENCE TO RELATED APPLICATIONS

This application is a national stage application under 35 U.S.C. § 371 of PCT Application No. PCT/US2018/027563, filed Apr. 13, 2018, which claims the benefit of U.S. Provisional Patent Applications Ser. No. 62/485,615 filed Apr. 14, 2017; and Ser. No. 62/500,633, filed May 3, 2017, which are hereby incorporated by reference in their entirety.

FIELD OF THE INVENTION

The present invention relates to a suturing device and methods of use thereof.

BACKGROUND OF THE INVENTION

The devices and techniques currently used for suturing are based on the devices and techniques used in sewing, i.e., the sharp tip of a needle to which a thread or suture is attached, generally by passing a portion of the leading end of the thread or suture through a small hole at the blunt end of the needle (i.e., the eye of the needle), is pushed into the material (fabric or tissue) being sewn or sutured by applying a force on the blunt end of the needle, forming a hole as it passes, until the needle emerges out of the material or tissue in another location; then the sharp end of the needle is grasped and pulled through the hole until it passes completely through, dragging the attached thread or suture behind the needle through the hole. This process is repeated to make multiple sutures or stitches. Thus, suturing requires either two hands or a sequential process of pushing the needle into a material followed by pulling the needle out of the material.

In laparoscopic and arthroscopic surgeries, where suturing is accomplished using an instrument (manual or robotic) inserted into the body of the patient that is controlled by a surgeon, this suturing process can be cumbersome and slow. The process often requires two different instruments, one for inserting the needle and another for drawing the needle out. There is a need for suturing tools that enable faster and easier suturing, preferably requiring only a single instrument.

In addition, there are circumstances where it is not desirable or it is very difficult or cumbersome to pass the needle through the tissue, and a tool that allows sutures to be made without fully piercing the tissue would be extremely useful. In other circumstances, such as when suturing in difficult to reach places within the abdomen, a suturing device that allows single-handed, rapid suturing would be extremely useful. In additional circumstances, such as on the battlefield or in clinics where sophisticated medical tools are unavailable and/or there is a need for speed, a simple, easy-to-use suturing device is needed.

Automatic and mechanical suturing devices, such as Covidien's Endo Stitch® and SILS® Stitch endscopic suturing devices, require a cumbersome means of passing a double-tipped needle back and forth between the two mandibles of a mechanical jaw, and require a fair amount of clearance to properly access a suture site. There is therefore also a need for suturing tools and techniques that can be mechanized or automated in a straightforward manner and into a more compact device appropriate for endoscopic surgeries.

The present invention is directed to overcoming these and other deficiencies in the art.

SUMMARY OF INVENTION

One aspect of the present invention relates to a suturing device including a hollow needle. The hollow needle has a length extending between a proximal end and a distal end and defining a lumen having an inner diameter. The suturing device further includes a length of surgical suture having a leading end and a trailing end and an outer diameter smaller than the inner diameter of the lumen. At least a portion of the surgical suture is located within the lumen of the hollow needle.

Another aspect of the present invention relates to a suturing kit including the suturing device of the present invention enclosed in packaging that maintains a sterile condition for the suturing device. The suturing kit further optionally includes a set of instructions.

Yet another aspect of the present invention relates to a method for suturing using the suturing device of the present invention. The method includes threading the leading end of the surgical suture into the lumen until a portion of the leading end of the surgical suture extends beyond the distal end of the hollow needle and the trailing end of the surgical suture is within the lumen or extends beyond the proximal end of the hollow needle. The surgical suture includes one or more self-retaining elements located along the length of the surgical suture and configured to engage a tissue when inserted therein to resist movement out of contact with the tissue. The hollow needle and a portion of the surgical suture are pushed into at least one tissue to create a hole in the at least one tissue. The hollow needle is pulled out of the at least one tissue without withdrawing the portion of the surgical suture from the hole in the at least one tissue.

A further aspect of the present invention relates to a laparoscopic apparatus. The laparoscopic apparatus includes a shaft having a lumen extending between a distal end and a proximal end. A handle comprising a lever is connected is connected to the proximal end of the shaft. A rod or wire having a distal end and a proximal end is disposed within the lumen of the shaft. The proximal end of the rod or wire is connected to the lever of the handle. The apparatus further includes the suturing device of the present invention including a sharpened tip and a proximal end. The suturing device is at least partially disposed within the lumen of the shaft at the distal end of the shaft and is connected at the proximal end to the distal end of the rod or wire. Movement of the lever in a first direction pushes the sharpened tip of the needle out of the lumen of the shaft and movement of the lever in a second direction pulls the sharpened distal of the needle into the lumen of the shaft.

The present invention provides a number of advantages including providing a suturing device that is a simple-to-use, versatile, and inexpensive device that enables rapid and easy one-handed suturing. The suturing device may be coupled to a moveable element that allows for mechanized suturing using the suturing device. A suturing kit and methods of suturing that include the suturing device of the present invention are also disclosed.

BRIEF DESCRIPTION OF THE DRAWINGS

FIG. 3 is a side perspective view of the exemplary suturing device with a bend near the distal end.

FIG. 4 is a side perspective view of the exemplary suturing device showing flexibility about angle A near the distal end.

FIG. 7 is a side perspective view of the exemplary suturing device with an external cutting edge at the distal end.

FIG. 8 is a side perspective view of the exemplary suturing device with an integral cutting edge at the distal end.

FIGS. 9A and 9B are side perspective views of the exemplary suturing device with a suture having a barb.

FIG. 10 is a side perspective view of the exemplary suturing device with a suture having a socket at a leading end thereof.

FIG. 13A-13E are schematic side views of the steps in an exemplary method of making a suture using the suturing device shown in FIG. 1.

FIG. 14A-14D are schematic views of exemplary types of sutures made using the suturing device shown in FIG. 1 to close a laceration or incision.

FIG. 15 is a schematic view of the exemplary suturing device having a chamber holding a liquid or viscous material and a sealed lumen of the needle.

FIG. 16 is a schematic view of exemplary suturing device suturing device shown in FIG. 1 incorporated into a syringe.

FIG. 18A is a perspective view of an apparatus for laparoscopic or endoscopic deployment incorporating the exemplary suturing device of the present invention in a retracted position.

FIG. 18B is a perspective view of the shaft of the apparatus for laparoscopic or endoscopic deployment shown in FIG. 18A incorporating the exemplary suturing device of the present invention in an extended position.

DETAILED DESCRIPTION OF THE INVENTION

The present invention relates to a suturing device and methods of use thereof.

One aspect of the present invention relates to a suturing device including a hollow needle. The hollow needle has a length extending between a proximal end and a distal end and defining a lumen having an inner diameter. The suturing device further includes a length of surgical suture having a leading end and a trailing end and an outer diameter smaller than the inner diameter of the lumen. At least a portion of the surgical suture is located within the lumen of the hollow needle.

Figure 1:
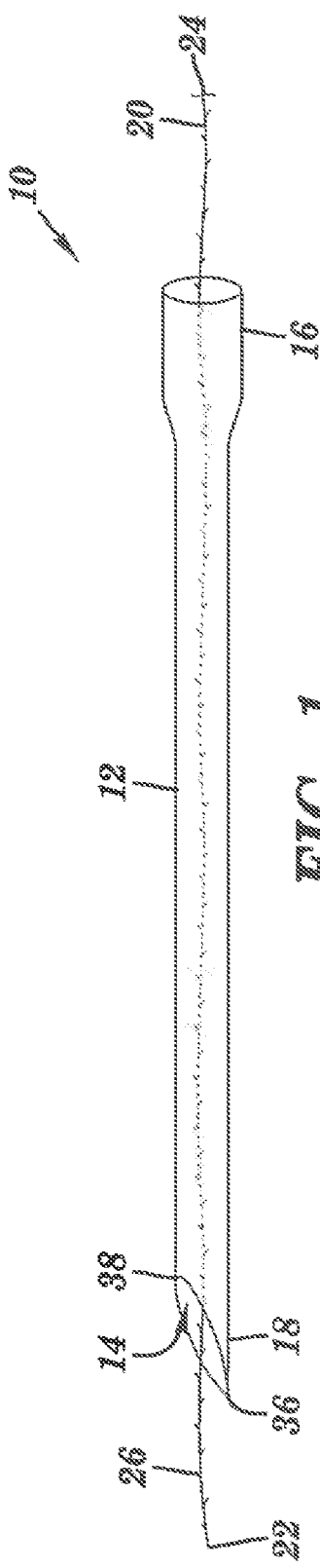
FIG. 1 is a side perspective view of an exemplary suturing device of the present invention.

FIG. 1 is a suturing device 10 that comprises a hollow needle 12 having a lumen 14 along a length of the hollow needle 12 extending between a proximal end 16 and a distal end 18. The proximal end 16 is blunt and the distal end 18 is configured for penetrating tissue. A length of self-retaining surgical suture 20 having a leading end 22 and a trailing end 24, is sized to fit within the lumen 14 of the hollow needle 12, while still being able to move axially within the lumen 14 (i.e., the outer dimensions of the suture 20 are smaller than the inner dimensions of the lumen 14 of the hollow needle 12). In one example, suture 20 is sized to fit within the lumen 14 and move relatively freely through the lumen 14 between the proximal end 16 and the distal end 18. The present invention provides a simple-to-use, versatile, and inexpensive device that enables rapid and easy one-handed suturing.

Referring again to FIG. 1, in an embodiment, the distal end 18 of the hollow needle 12 is beveled forming an elliptical opening in the distal end 18 of the hollow needle 12. The most distal portion of the elliptical opening is a sharpened tip 36 suitable for penetrating and/or cutting into tissue. In this example, the most proximal end 38 of the elliptical opening of the beveled tip (i.e., the part closest to the proximal end 16 of the hollow needle 12) forms a sharp edge where the opening and inner wall of the lumen 14 intersect. In another example, the most proximal end 38 of the elliptical opening is rounded, which reduces the likelihood that the portion of the suture 20 passing through the suturing device 10 of the present invention will inadvertently be damaged by a sharp edge as the hollow needle 12 is being pushed into tissue. In another example, the most proximal end 38 of the elliptical opening of the beveled tip is roughened or corrugated to increase friction between the most proximal end 38 and the suture 20, thereby increasing the drag on the suture 20 and therefore the tension applied by the needle 12 to the portion 25 and/or 27 (referring to FIG. 12) of the suture 20 external to the lumen 14 of the hollow needle 12 when in use as described in further detail below.

Figure 2:
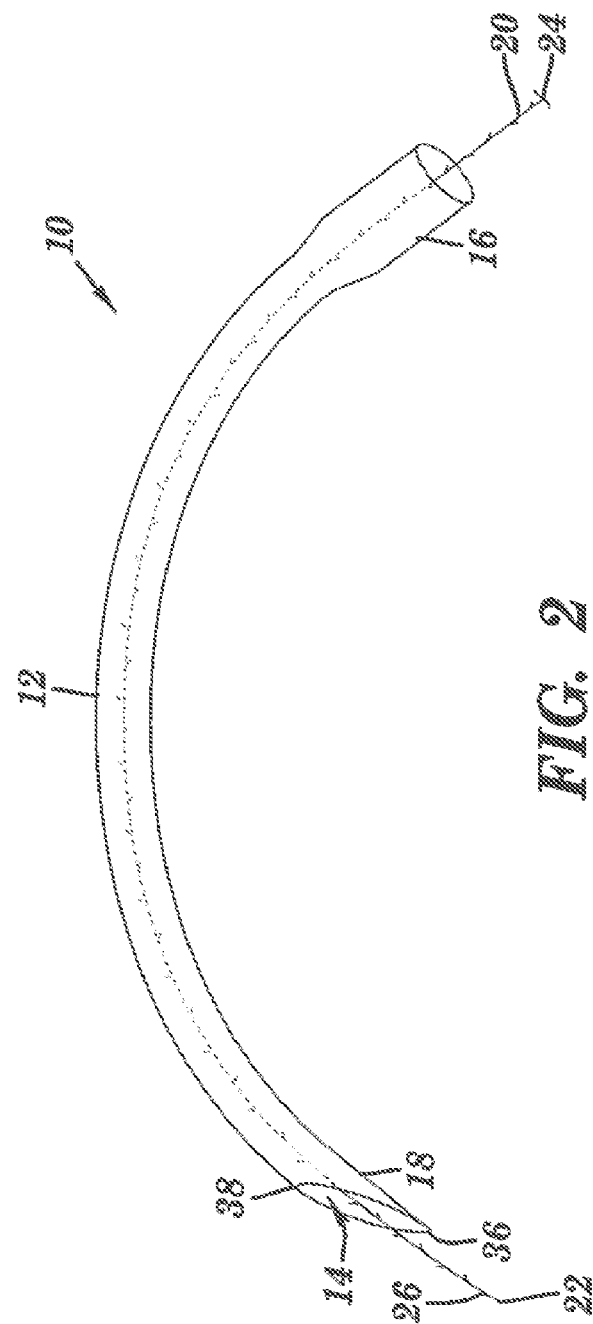
FIG. 2 is a side perspective of the exemplary suturing device with a curved hollow needle.

The hollow needle 12 can have the external shape, size, and dimensions, including any length, of any needle currently used for suturing, and of any needle created for suturing in the future. The hollow needle 12 of the suturing device 10 can be straight, bent, helical, or curved, with the curvature of any curved needle having a single radius or multiple radii. Referring now to FIG. 2, an example of suturing device 10 is illustrated in which the hollow needle 12 is curved. In one example, the curvature of the hollow needle 12 is configured such that the hollow needle 12 can be hooked into the tissue and embedded by pulling on the proximal end 16.

Referring now to FIG. 3, another example of suturing device 10 is illustrated. In this example, the distal end 18 of the hollow needle 12 has an elbow 28 that orients the distal end 18 or sharpened tip 36 of the hollow needle 12 to allow easy suturing of the wall of a lumen, such as the urethra, stomach, or intestines, such as at a 45 degree, 60 degree, 75 degree, or 90 degree angle to the longitudinal axis of the proximal end 16 of the hollow needle 12. In an embodiment as illustrated in FIG. 4, the angle (A) of the portion of the hollow needle 12 proximate to the distal end 18 is adjustable at the elbow 28. An adjustable-angle (A) needle may be useful where the suturing device 10 is delivered through a lumen in the body using an endoscopic device so that the angle (A) can be adjusted once the suturing device 10 is in the right location to allow it to suture in the wall of the lumen. In an embodiment, the hollow needle 12 is rigid. In another embodiment, the hollow needle 12 is flexible.

Referring now to FIG. 7, in an embodiment, the suturing device 10 comprises a cutting edge 40 proximal to the distal end 18 of the hollow needle 12. In an embodiment, as shown in FIG. 7, the cutting edge 40 is situated on the external wall of the hollow needle 12, aligned with the longitudinal axis of the hollow needle 12. Referring now to FIG. 8, in an alternate embodiment, the cutting edge 40 is located within a notch in the opening at the distal end 18 of the lumen 14 of the hollow needle 12. In another example, the needle 12 may incorporate a cutting tool within the lumen 14 which can be extended down towards the distal end 18 of the needle 12 and used to cut the suture 20 when the suturing is complete.

In another embodiment, the hollow needle 12 has a base that is either an integral part of the hollow needle 12 or an attachment thereto, and the base incorporates a cutting tool. In one embodiment, the base has a notch whose opening is sufficiently wide that the suture 20 can fit within it and which has a cutting edge within it, either at its base or along one of its sides. In use, the notch is used to first grab or capture the suture 20, and then by moving the suturing device 10 so that the suture 20 is pressed against the cutting edge, to cut the suture. The notch may have tapered sides, one of which is a cutting edge. The base may have a lumen through which the suture 20 can pass into the lumen 14 of the hollow needle 12, or there may be a hole in the wall of the hollow needle 12 away from the sharp tip through which the suture 20 can exit the lumen 14 of the hollow needle. In another embodiment, there is a sleeve over a portion of the proximal end of the hollow needle 12 which has a cutting notch incorporated into it.

Figure 5:
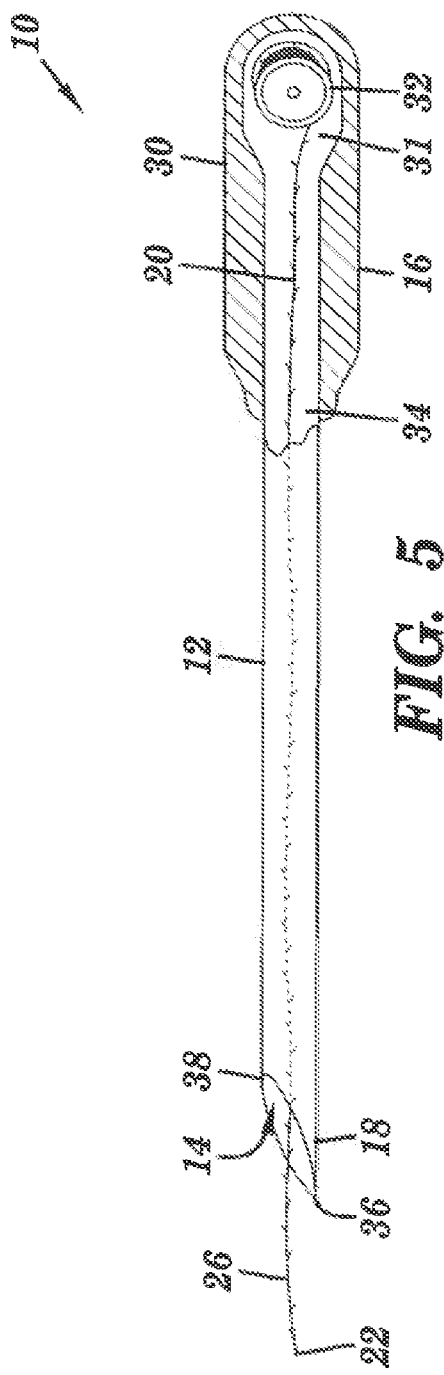
FIG. 5 is a side perspective view of the exemplary suturing device with a base at the proximal end.

Referring now more specifically to FIG. 5, in one embodiment, the hollow needle 12 of the suturing device 10 may be affixed at or proximal to the proximal end 16 to a base 30. The base 30 can be configured to make manipulation of the hollow needle 12 easier or for making it easier to push the hollow needle 12 into tissue and/or for withdrawing the hollow needle 12 from tissue, as described with respect to the operation of the suturing device 10 as further described below. Any base 30 or other grip incorporated into or adapted for use with any suturing or other needle (e.g., I.V. needle) currently available or that becomes available in the future can be adapted to the suturing device 10 of the present invention.

The base 30 is not intended to enter the tissue and can therefore have a larger outer diameter than the hollow needle 12. The base 30 can be made of various materials, such as metal or polymer, preferably surgical-grade. The hollow needle 12 can be permanently affixed to the base 30 or removably attached, such as by a friction fitting or threaded connection. The base 30 may serve as a grip and may contain, such as in examples as shown in FIGS. 5, 15 and 16, a chamber 31.

In an embodiment, a portion of the leading end 22 of the suture 20 is positioned within the lumen 14 of the hollow needle 12. In another embodiment, a portion of the leading end 22 of the suture 20 extends beyond the distal end 18 of the hollow needle 12 as shown in FIG. 1. In yet another embodiment, a portion of the suture 20 is positioned within the lumen 14 of the hollow needle 12, and the leading end 22 of the suture 20 extends beyond the distal end 18 of the hollow needle 12, and the trailing end 24 extends beyond the proximal end 16 of the hollow needle 12.

In use, the leading end 22 of the suture 20 extends out of the distal end 18 of the lumen 14 of the hollow needle 12. In one example, the suture 20 is a unidirectional self-retaining suture having barbs 26, although other types of suture may be utilized with the present invention. In this example, the barbs 26 are oriented within the lumen 14 such that when the leading end 22 of the suture 20 is inserted into a patient's tissue with the leading end 22 first, the barbs 26 engage with the tissue when tension is exerted on the trailing end 24 of the suture 20 and resist movement out of contact with the tissue to prevent the leading end 22 of the suture 20 from being pulled out of the tissue. The barbs 26 are oriented within the lumen 14 such that if the lumen 14 were a hole in the tissue, the barbs 26 would resist movement towards the proximal end 16 of the hollow needle 12 (i.e., resist tension applied to the trailing end 24 of the suture 20).

Referring again to FIG. 1, the self-retaining suture 20 of the present suturing device 10 can be bi-directional (e.g., Quill SRS®, Angiotech) or unidirectional (e.g., V-Loc®, Covidien), have an adhesive coating or roughened external surface, be made of a material that does not slip easily through tissue, or be any other type of suture that resists movement of the suture 20 through tissue in at least one direction. The resistance force of the self-retaining suture 20 must be sufficient to draw additional portions of the suture 20 through the lumen 14 of the hollow needle 12. The suture 20 must also resist being pulled out once embedded in a hole in tissue created by the hollow needle 12 during the suturing process. Under certain circumstances, standard suture may be used in the suturing device 10 of the present invention. In one example, the suture 20 is made from an absorbable polymer, such as polydioxanone, PDO; a polyglycolidepoly-e-caprolactone copolymer, Monoderm; or polylactic acid, by way of example only, so that it can be left in place, but the suture 20 can also be a nonabsorbable formulation, such as polypropylene or nylon by way of example only. In one example, the suture 20 is made from a biocompatible material.

In an example, the outer dimension of the suture 20 and the inner dimension of the lumen 14 of the hollow needle 12 are sized such that the force necessary to cause the suture 20 to slide through and move longitudinally within the lumen 14 is less than the anchoring force of the self-retaining suture 20 in a hole in the tissue made by the hollow needle 12 (i.e., less than the force required to pull the self-retaining suture 20 out of the tissue when oriented to resist such movement in the direction of the pulling force).

In a further embodiment, the leading end 22 of the suture 20 is larger than the distal opening of the lumen 14 of the hollow needle 12 which prevents the leading end 22 from being pushed back into the lumen 14 when the hollow needle 12 is first inserted into tissue. In another embodiment, the leading end 22 has barbs 26 or similar structures (like the barb on a fishing hook or harpoon) which engage with the tissue wall of the hole made as the hollow needle 12 is inserted into the tissue and anchor the leading end 22 of the suture 20 in the hole so that it resists being pulled out of the tissue as the hollow needle 12 is being retracted.

Referring now to FIGS. 9A and 9B, in a further embodiment, the leading end of the suture 20 has the equivalent of a barb 42 attached to the leading end 22 that serves as a sharpened tip that can easily penetrate into tissue but which is designed to resist extraction as shown in FIG. 9B. In one example, the barb 42 is made of a biocompatible, absorbable material. FIG. 10 illustrates an example with the suture 20 having a socket 44 at the leading end 22 thereof.

In one embodiment, the chamber 31 at the proximal end 16 of the hollow needle 12 stores extra suture 20. Referring again to FIG. 5, in one example the chamber 31 in base 30 holds a spooling element 32 holding excess suture 20. Alternatively, the base 30 may be situated between a separate grip and/or chamber 31 and the hollow needle 12. The suture 20 passes from the chamber 31 into the lumen 14 of the hollow needle 12 at its proximal end 16 through an opening in the wall of the chamber 31 into the lumen 14 of the hollow needle 12 and passes through the lumen 14 of the hollow needle 12 and out its distal end 18. In an embodiment, the chamber 31 is located within the grip or base 30 as shown in FIG. 5.

Figure 6:
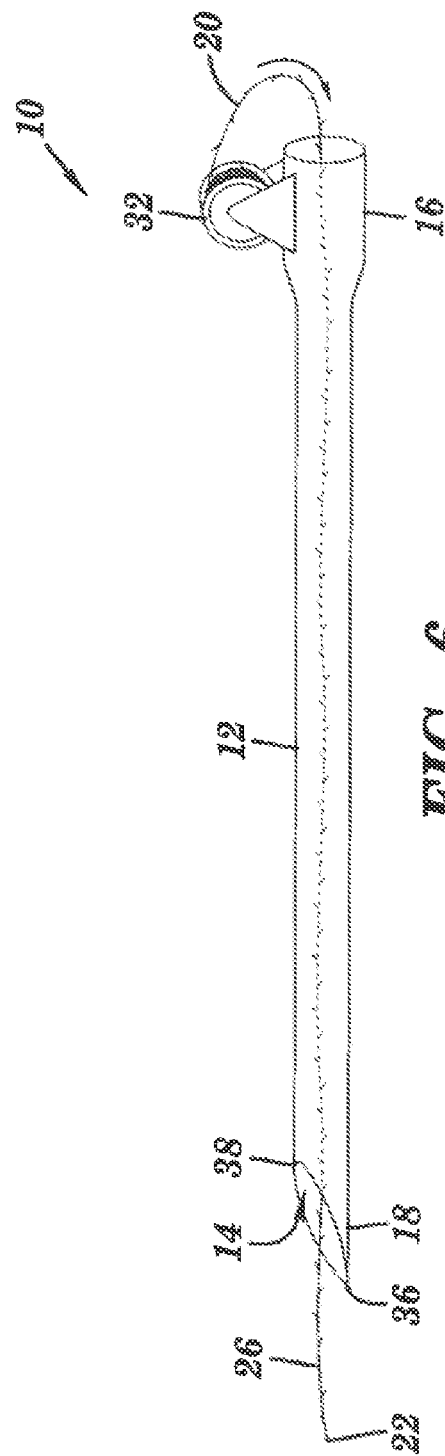
FIG. 6 is a side perspective view of the exemplary suturing device with an external spooling device.
Figure 12:
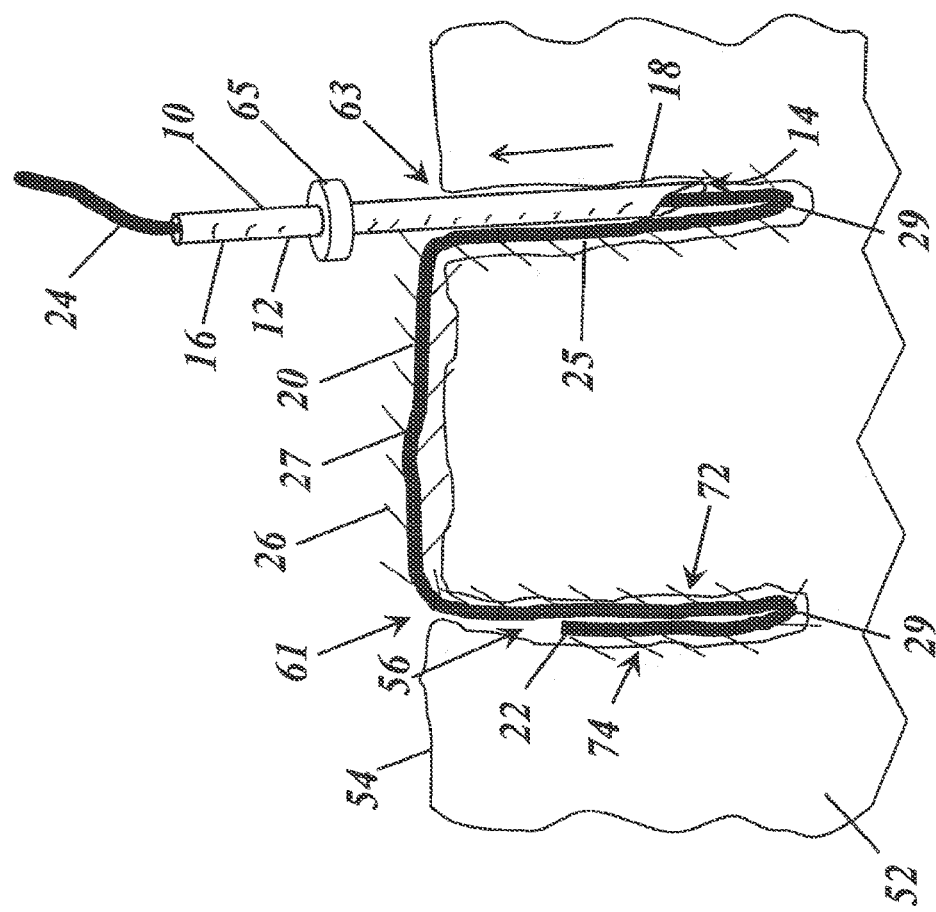
FIG. 12 is a cutaway schematic view of the cross-section of a suture made using the suturing device shown in FIG. 1 showing orientation of and engagement with tissue of the barbs of a unidirectional self-retaining suture.

In another embodiment, the trailing end 24 of the suture 20 and the extra suture is wound around the spooling element 32 located in the chamber 31, such as a cylinder or wheel, which is inside the chamber 31. Alternatively, as shown in FIG. 6, the spooling element 32 may be located outside of the hollow needle 12. In either embodiment, the force necessary to cause the suture 20 to be pulled out of the chamber 31, including in certain embodiments, off the spooling element 32, and through the lumen 14 must be less than the anchoring force of the self-retaining suture 20 in a hole in flesh made by the hollow needle 12. If the outer dimensions of the chamber 31 are larger than the outer diameter of the needle 12, the chamber 31 may serve the function of preventing the needle 12 from being inserted farther than a certain distance into tissue (i.e., the same function as the optional flange as shown in FIG. 12 as described further below).

Referring now to FIGS. 5 and 15, the chamber 31 may enclose both extra suture 20 and a liquid or viscous material 34. The liquid or viscous material 34 can be an active agent or gel or saline, such as a hemostatic agent to stop bleeding (e.g., epinephrine, clotting factors etc.). In this example, the liquid or viscous material 34 is also present in the lumen 14 of the hollow needle 12 which is fluidically connected to the chamber 31.

In one example, the distal end 18 of the lumen 14 is sealed to prevent the liquid or viscous material 34 from leaking out prior to the first suture, such as by a plug or seal 45 (as shown in FIG. 15). In this example, the suture 20 may extend through the plug or seal 45 so that a portion of the leading end 22 of the suture 20 is exposed. The plug or seal 45 may be a gel or polymeric or a wax or another material capable of forming a leak-proof seal with the inner walls of the lumen 14 and the suture 20. The seal formed by plug or seal 45 must be strong enough to resist leaking but not so strong as to prevent the suture 20 from being drawn out of the lumen 14 when the hollow needle 12 is first inserted into the tissue being sutured. As the suture 20 is drawn out of the lumen 14 and chamber 31, the seal formed by the plug or seal 45 is broken or pulled out of the lumen 14 of the hollow needle 12, and the suture 20 draws the liquid or viscous material 34 with it, coating the suture 20 as it passes through the lumen 14 and before it enters and traverses the tissue. In an embodiment, the plug or seal 45 is a valve or valve mechanism, preferably one through which the suture 20 passes without allowing liquid or viscous material 34 on one side to leak or otherwise escape to the other side unless the suture 20 is being pulled through the valve. A stretched rubber seal with a hole that opens only when under pressure can also serve, such as by being stretched across the opening from the chamber 31 into the lumen 14 of the needle 12.

Another aspect of the present invention relates to a method for suturing using the suturing device of the present invention. The method includes threading the leading end of the surgical suture into the lumen until a portion of the leading end of the surgical suture extends beyond the distal end of the hollow needle and the trailing end of the surgical suture is within the lumen or extends beyond the proximal end of the hollow needle. The surgical suture includes one or more self-retaining elements located along the length of the surgical suture and configured to engage a tissue when inserted therein to resist movement out of contact with the tissue. The hollow needle and a portion of the surgical suture are pushed into at least one tissue to create a hole in the at least one tissue. The hollow needle is pulled out of the at least one tissue without withdrawing the portion of the surgical suture from the hole in the at least one tissue.

An exemplary operation of the suturing device 10 will now be described with respect to FIGS. 1, 12, and 13A-E. By way of example only, the suturing device 10 may be utilized in the following procedures: male or female urethroplasty, bladder neck reconstruction, graft suturing (including skin grafts or oral grafts), vaginoplasty, endoscopic treatments (including bladder ruptures or lacerations), plastic surgery applications (including grafts), closing external wounds or lacerations, suturing bleeding lesions (colon, stomach, intestines), securing mesh during hernia repair (open or laparoscopic). These procedures are merely exemplary and the suturing device 10 can be used in any other procedures where suturing is required.

To use the suturing device 10 of the present invention, the hollow needle 12 of the suturing device 10 is first inserted into a tissue 52 through a surface 54 of the tissue 52. The suturing device 10 is inserted into the tissue 52 an appropriate distance (e.g., 0.1-25 mm inclusive) creating a puncture hole 56 and embedding a portion 25 of the leading end 22 of the suture 20 in the tissue 52 (this will typically be accomplished by applying a force aligned with the longitudinal axis of the hollow needle 12 in the direction of the distal end 18 of the hollow needle 12), as shown in FIG. 12.

In the embodiments shown in FIGS. 12, 13A-E and 14, the suture 20 passes into and through the lumen 14 of the hollow needle 12, with a leading end 22 extending beyond the distal end 18 of the needle 12 and a trailing end 24 optionally extending beyond the proximal end 16 of the needle 12. Insertion of the hollow needle 12 into the tissue 52 can be accomplished manually or mechanically, and employ manual, electrical, hydraulic, pneumatic or any other types of motive force. For example, the suturing device 10 can be attached to a linear actuator or motor or to a piston driven pneumatically, electrically or hydraulically.

As the hollow needle 12 is inserted into the tissue 52, the exposed portion of the suture 20 extending beyond the distal end 18 of the lumen 14 of the hollow needle 12 will fold back along the hollow needle 12 and come into contact with the tissue wall of the puncture hole 56 being created by the hollow needle 12.

In one example, the suture 20 is a self-retaining suture that resists movement of the exposed portion of the suture 20 into the tissue 52, thereby exerting tension on the suture 20 which draws additional portions 25 of the suture 20 out of the distal end 18 of the lumen 14 of the hollow needle 12, although in some cases the force pulling the suture 20 into the puncture hole 56 may overcome this resistance and drag the leading end 22 of the suture 20 into the hole 56. In the example of a suturing device 10 incorporating suture 20 as a unidirectional suture as shown in FIG. 12, the barbs 26 of the unidirectional self-retaining suture 20 are oriented so that they will engage with (e.g., catch on) the tissue 52 at an engagement location 74 when the suture 20 is pulled downwards into the tissue 52 by the distal end 18 of the hollow needle 12 (the width of the hole 56 shown in FIG. 12 is exaggerated for purposes of illustration). At the distal end 18 of the hollow needle 12, the direction of the suture 20 changes 180 degrees as the suture 20 bends at bend location 29 into the lumen 14 of the hollow needle 12. On one side of the bend location 29, an exposed portion 25 of the suture 20 extends up along the side of the hollow needle 12 external to the lumen 14 of the hollow needle 12 while on the other side of the bend location 29, the suture 20 extends up into the lumen 14 of the hollow needle 12.

In the example as shown in FIG. 12, a stop or flange 65 is situated along the length of the hollow needle 12. The stop or flange 65 functions as a stop to determine the depth to which the needle 12 can be inserted into the tissue 52 without depressing the surface 54 of the tissue 52. In an embodiment, the position of the stop or flange 65 is adjustable. The stop or flange 65 makes consistency of sutures easier to maintain. In another embodiment, the suturing device 10 has markings or color coding along its length (such as millimeter or fractions of centimeters or inches, by way of example) that indicate how far the needle 12 has been inserted into the tissue 52. In one example, the optimal depth for the particular suturing device 10 may be indicated with a distinctive marking.

Next, the hollow needle 12 is withdrawn from the puncture hole 56 it has created by pulling on the hollow needle 12 in the opposite direction, away from the tissue surface 54. When the direction of the hollow needle 12 is changed and the hollow needle 12 is withdrawn, the exposed portion 25 of the suture 20 in the puncture hole 56 will resist being withdrawn, and will exert tension on the suture 20 that will draw additional portions of the suture 20 out of the lumen 14 through the distal end 18 of the hollow needle 12. The barbs 26 of the additional portions of suture 20 will engage such as at engagement location 72 with the tissue 52 along the path of the hollow needle 12 as it is withdrawn from the puncture hole 56 in the tissue 52 and continue to apply tension on the suture 20 that draws more of the suture 20 out of the lumen 14 of the hollow needle 12. In this example, the barbs 26 of the unidirectional self-retaining suture 20 are oriented such that they both resist movement of the exposed portion 25 of the unidirectional suture 20 into the puncture hole 56 created by the hollow needle 12 as it is inserted into the tissue 52 and movement of the additional portion of the unidirectional suture 20 out of the puncture hole 56 as the hollow needle 12 is withdrawn from the tissue 52.

After the hollow needle 12 is withdrawn, a loop of suture 20 will remain embedded (anchored) in the puncture hole 56 in the tissue 52 formed by the hollow needle 12, with the leading end 22 of the suture 20 descending into the hole 56 to the bend location 29 and another portion of suture 20 continuing beyond the bend location 29 until it exits the puncture hole 56 and, in use, enters the lumen 14 of the hollow needle 12 (note that the first time the suture 20 is embedded into the tissue 52, the leading end 22 may be completely buried, as shown in FIG. 12, or a loose tail may extend above the surface 54 of the tissue 52, as shown in FIG. 13B-E).

After embedding a portion of the suture 20 in a first puncture hole 56, each time the hollow needle 12 is repositioned and re-inserted into the tissue 52 at a new location, such as second insertion site 63 as shown in FIG. 12, additional portions of the suture 20 will be drawn out of the distal end 18 of the lumen 14 of the hollow needle 12, leaving behind a series of embedded loops at bend locations 29 with a portion 27 of the suture 20 extending across the surface 54 of the tissue 52 between the embedded loops at the bend locations 29.

Figure 13D:
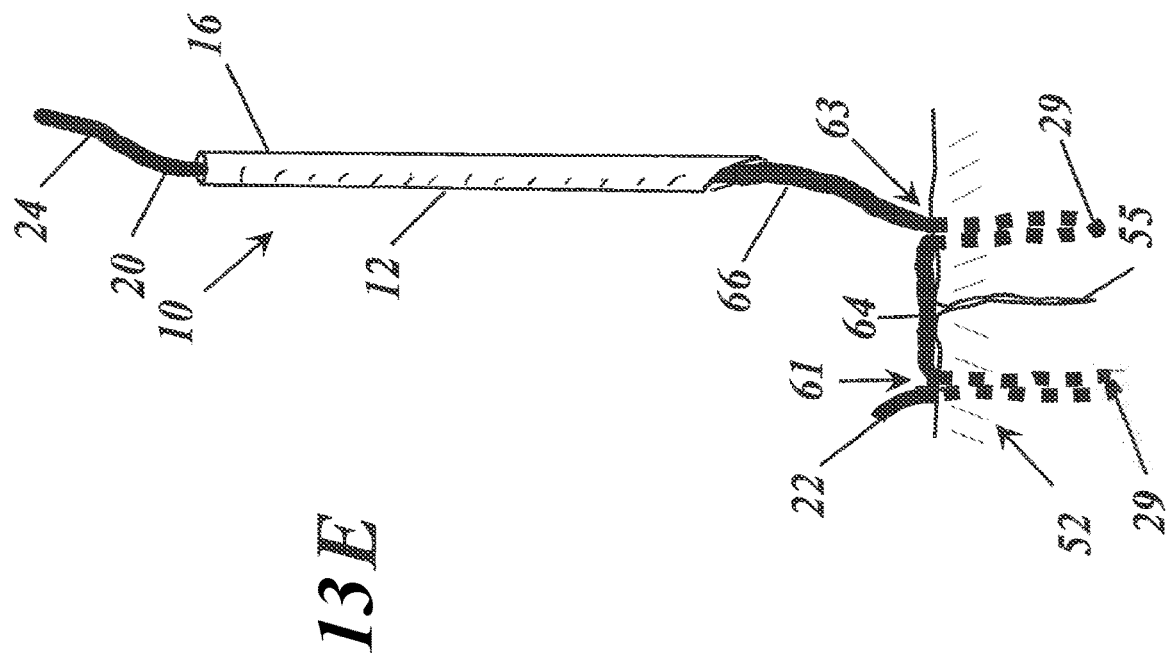

FIGS. 13A-E show the same sequence of steps when suturing across a laceration 55. In this example, the self-retaining feature of the suture 20 is not shown. FIG. 13A shows the hollow needle 12 with the sharpened tip 36 about to penetrate through the outer surface 54 of the tissue 52 to one side of the laceration or incision 55 (e.g., a laceration in skin) at a first insertion site 61. A leading portion 62 at the leading end 22 of the suture 20 is outside of the lumen 14 of the hollow needle 12.

FIG. 13B shows the hollow needle 12 after it has penetrated the tissue 52 at the first insertion site 61, with the leading portion 62 of the suture 20 remaining outside of the needle 12 and partially embedded in the puncture hole created by the needle 12 in the tissue 52 (dotted line) and partially outside of the tissue 52 (solid line).

FIG. 13C shows the hollow needle 12 after it has been withdrawn from the tissue 52, leaving a loop at the bend location 29 of suture 20 embedded in the tissue 52. A new portion 64 of suture 20 has been drawn out of the lumen 14 of the hollow needle 12.

FIG. 13D shows the hollow needle 12 inserted into the tissue 52 at a second insertion site 63 on the other side of the laceration 55, which has been pulled closed. The new portion 64 of suture 20 extends across the laceration 55, from the first insertion site 61 of the hollow needle 12 to the second insertion site 63 of the needle 12.

Figure 13E:
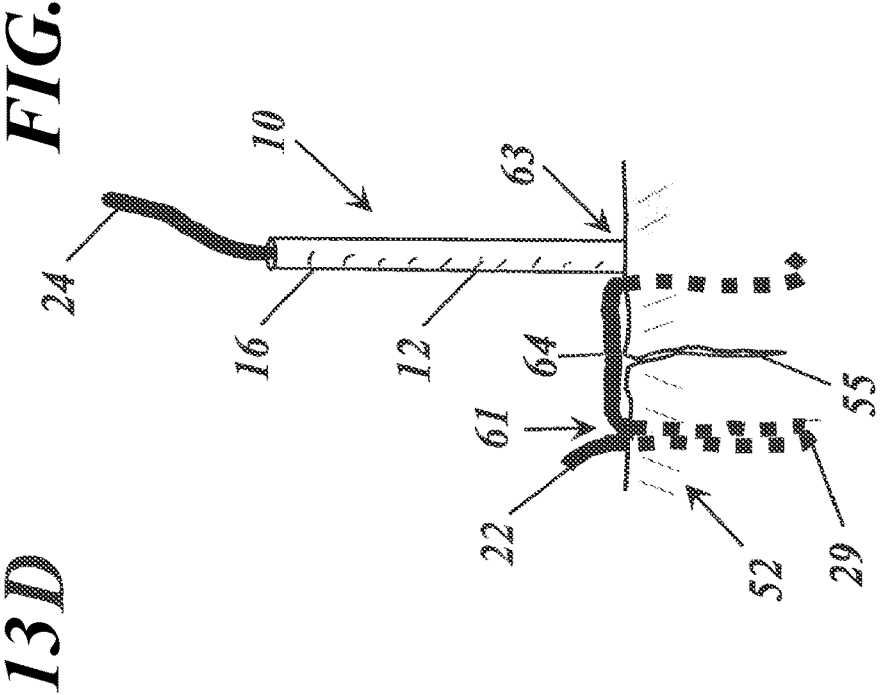

FIG. 13E shows the hollow needle 12 after it has been withdrawn from the puncture hole created at the second insertion site 63 and left behind a second loop or bend location 29 of suture 20 embedded in the puncture hole formed by the needle 12 in the tissue 52. If closing the laceration 55 requires more than a single stitch, additional stitches alternating from one side of the laceration 55 to the other, or using some other pattern, can be made. By way of example, the needle 12 may be inserted into the tissue 52 orthogonal to the surface 54 or at an angle, and if at an angle, with the needle 12 inserted parallel to the plane of the laceration, the plane of the laceration being orthogonal to the surface 54 of the tissue and parallel (or tangential) to the laceration 55, angled towards the plane of the laceration 55, or angled away from the plane of the laceration 55.

The suturing device 10 of the present invention can be used to close a laceration or incision by suturing into the incision or laceration from a single side of the wound. It can also hold the two sides of a laceration or incision together below the surface of the tissue. FIGS. 14A and 14B illustrate two exemplary suturing stitches that can be done using the suturing device 10 of the present invention. FIG. 14A shows the hollow needle 12 after it has been inserted into tissue 52 at an oblique angle and then pulled out of the tissue 52. The needle 12 creates a puncture hole (not shown) which passes from one side of the laceration 55 to the other, leaving a loop of suture at bend location 29 embedded in the tissue 52 and holding the two sides of the laceration 55 together. To close a laceration requiring more than a single stitch, a person may suture from a single side of the laceration 55 or alternate from one side of the laceration 55 to the other, always entering the tissue 52 with the needle 12 angled towards the plane of the laceration 55.

In FIG. 14B, the needle 12 was inserted into the tissue 52 at an oblique angle into and through the laceration 55, after which it was repositioned so that it would exit the tissue 52 on the other side of the laceration 55, and then the needle 12 was withdrawn. A loop or bend location 29 of suture 20 is external to the tissue 52. In one example, a suturing device with a curved needle, such as those shown in FIGS. 2 and 3, could be used to make the suture stitch shown in FIG. 14B.

As shown in FIG. 14C, the suturing device 10 can also be used to tack one piece of tissue (e.g., a graft) to another simply by passing the hollow needle 12 through both pieces of a first tissue 93 and a second tissue 94 to embed a suture 'tack' that holds the two together. In this example, the first tissue 93 may be an upper tissue and the second tissue 94 may be a lower tissue, although these directions are merely indicated for illustration purposes. To tack the first tissue 93 (e.g., a graft) to the second tissue 94, the needle 12 of the suturing device 10 is inserted into and through the first tissue 93 into the second tissue 94.

FIG. 14C shows three embodiments of the 'tack.' In a first embodiment, the single tack 151 is a separate piece of suture 20 forming a loop at bend location 29 that is embedded in the two tissues. The suture 20 is embedded as described above. The trailing end 24 of the suture 20 can be trimmed after the tack is made, or the suture 20 can be sized specifically to make single tack 151. Both the leading end 22 and the trailing end 24 of the suture 20 will be exposed. In this example, the self-retaining suture 20 will engage with both the first tissue 93 and the second tissue 94, holding them together. In this example, the suture 20 may not extend through the entire lumen 14 of the hollow needle 12, but be held in the needle 12 by friction between the suture 20 and an inner wall of the lumen 14 of the needle or by a plug of some sort similar to the seal 45 shown in FIG. 15.

In other embodiments, the tack 152 and suture tack 153 are a single length of suture with a barb 42 at the leading end 22 such as that shown in FIGS. 9A and 9B. The suture is of an appropriate length to hold the first tissue 93 and the second tissue 94 together—i.e., long enough to be sufficiently anchored in the second tissue 94 while still engaging sufficiently with the first tissue 93 to hold it in place. The suture 20 in the tack 152 is self-retaining suture that resists movement, for example, in either direction.

In an embodiment as shown in FIG. 14D, the suture 20 is a unidirectional suture with barbs 26 oriented to resist movement of the suture 20 into the tissue; this will resist movement of the first tissue 93 away from the second tissue 94, provided the suture 20 remains fixed in position relative to the second tissue 94. When the needle used to make the 'tack' is withdrawn, the barb 42 at the leading end 22 of the suture 20 will anchor itself in the second tissue 94, preventing it from being pulled out of the second tissue 94, and pulling the rest of the suture 20 out of the lumen 14 of the needle 12, thereby exposing the barbs 26. The exposed barbs 26 will resist movement of the first tissue 93 away from the second tissue 94. The tack 152 or suture tack 153 may be made with a short piece of suture 20 or by cutting the suture 20 after the needle 12 is withdrawn from the first tissue 93 and the second tissue 94.

In an embodiment, only the trailing end 24 of the suture 20 is unidirectional self-retaining suture oriented to prevent movement of the first tissue 93 away from the second tissue 94. The leading end 22 of the suture 20 proximal to the barb 42 can be a bidirectional self-retaining suture, unidirectional suture with its barbs oriented to prevent movement of the suture out of the tissue (i.e., away from the barb 42), or a regular suture. In an embodiment as shown in FIG. 14C, the suture tack 153 has a flange or stop 43 on the trailing end 24. The stop 43 is sized to fit within the lumen 14 of the hollow needle 12 of the suturing device 10 used; it may be advisable to have a flange along the length of the needle 12 (such as the one shown in FIG. 12) to ensure that the needle 12 will be inserted into the tissue a distance that will result in the stop 43 being at the surface of the first tissue 93. As the needle 12 is withdrawn, the stop 43 will be outside of the first tissue 93, and the puncture made by the needle 12 will close around the suture 20.

Referring again more specifically to FIG. 12, although the hollow needle 12 can penetrate entirely through the tissue 52, this is not necessary, and in many or most cases, the hollow needle 12 will stop short of full penetration, leaving a puncture hole 56 with a single opening or exit. The distance that the hollow needle 12 must penetrate into the tissue 52 in order for the suture 20 being used to become anchored in the tissue 52 is a function of the type of suture 20 used and its size and the medical issue that the suturing is addressing. An optional external flange on the needle 12 can prevent the needle 12 from being inserted too far into tissue 52, and the optional external flange and/or optional external markings can indicate the proper distance the needle 12 should be inserted.

Referring now to FIG. 16, in an embodiment, the chamber 31 of the suturing device 10 is a syringe barrel 69. In this embodiment, there is a lumen 14 in the hollow needle 12 through which the suture 20 passes (the dotted portion is within the lumen 14 or chamber 31), and the lumen 14 is fluidly connected to the syringe barrel 69 such that suture 20 in the chamber 31 can pass from the chamber 31 into the lumen 14 (in a syringe, the connection between the needle and the barrel is called the hub).

An element 46 external to the syringe barrel 69 enables a plunger 47 to be depressed to expel the liquid or viscous material 34 from the syringe barrel 69. There may be excess suture 20 in the barrel of the syringe, such as, for example, suture 20 that is loose or spooled in some way. When the plunger 47 of the syringe is depressed, the liquid or viscous material 34 within the syringe barrel 69 will be forced into and through the lumen 14 of the hollow needle 12 toward the distal end 18, from whence it will be expelled. In an embodiment, the needle 12 is removably attached or permanently affixed to the syringe barrel 69.

In an embodiment, spooling element 32 prevents the suture 20 within the syringe barrel 69 from being expelled with the liquid or viscous material 34 by providing a resistive force (for example, the spooling element 32 has a braking mechanism [not shown] that prevents the spooling element 32 from turning under the tension created by the liquid or viscous material 34 on the suture 20 as it is being pushed into and out of the lumen 14). In this example the resistive or friction force is less than the holding force of the suture 20 in tissue, and so the suture 20 can be drawn off the spooling element 32 during the suturing process described elsewhere herein.

Optionally, a port 71 is fluidly connected to the syringe barrel 69 that allows the introduction of the liquid or viscous material 34 into the syringe barrel 69 (the excess suture 20 is preferably within the syringe barrel 69, and the seal 45 is optionally already positioned in the lumen 14 of the hollow needle 12, and there may be no liquid or viscous material 34), or the introduction of another reagent or additive to liquid or viscous material 34 already in the syringe barrel 69.

The plunger 47 can be operatively connected to an element 46 which can, in various embodiments, be a manual grip, a pad a user can push on (such as is typical of manual syringes), or a driving mechanism (such as a driving mechanism 83 as shown in FIG. 17, with the plunger 47 serving as the movable element 85 as also shown in FIG. 17, and with the driving mechanism attached to a base [not shown]). In the latter embodiment, the driving mechanism may be in electrical or other communication with the spooling element 32 or a sensor in the needle (not shown) so that the depressing of the plunger 47 can be both automated and synchronized with the dispensing of the suture 20 (i.e., as more of the suture 20 exits the distal end 18 of the needle 12, more liquid or viscous material 34 is expelled from the syringe barrel 69 into the lumen 14 of the hollow needle 12. The suturing device 10 optionally has a flange 73 such as those commonly incorporated into manual syringes, the flange 73 situated at the opposite end of the syringe barrel 69 from the needle 12. Like in a typical syringe, a portion of the plunger 47 passes through the wall of the syringe barrel 69 and into the syringe barrel 69.

In an alternate embodiment of the suturing device 10 shown in FIGS. 5 and 15, the chamber 31 is a bulb (e.g., the chamber has flexible walls) which can be squeezed to expel the fluid or viscous material 34 from the chamber 31 out through the lumen 14 of the hollow needle 12. There may be excess suture 20 in the bulb.

Figure 17A:
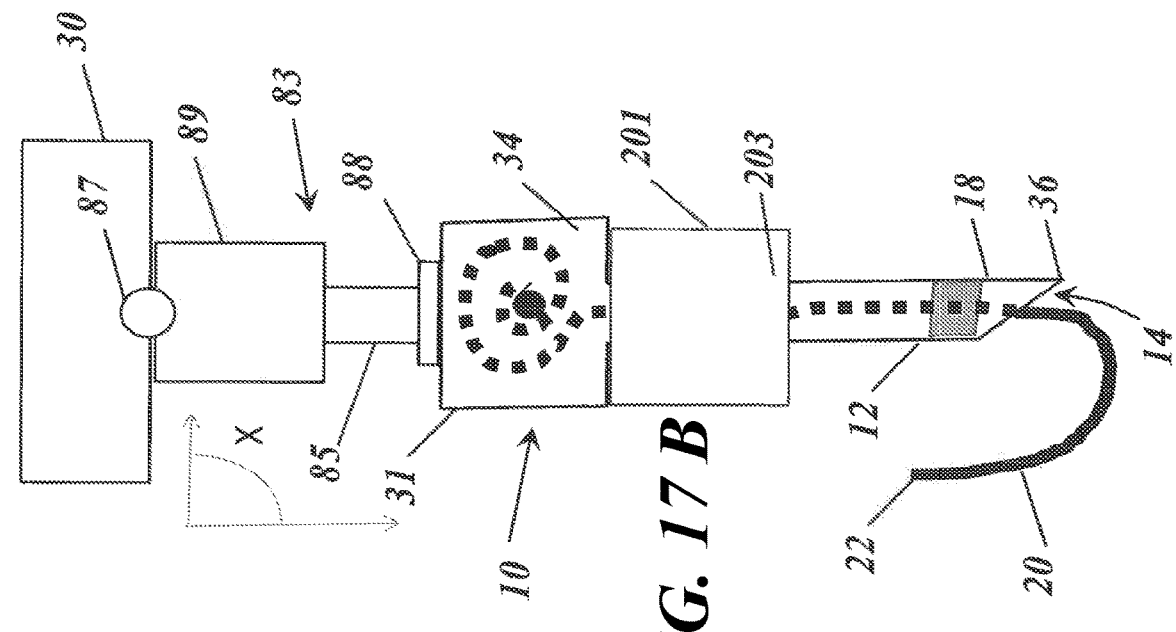
FIGS. 17A and 17B are schematic views of a mechanized suturing device including the exemplary suturing device shown in FIG. 1.
Figure 17B:
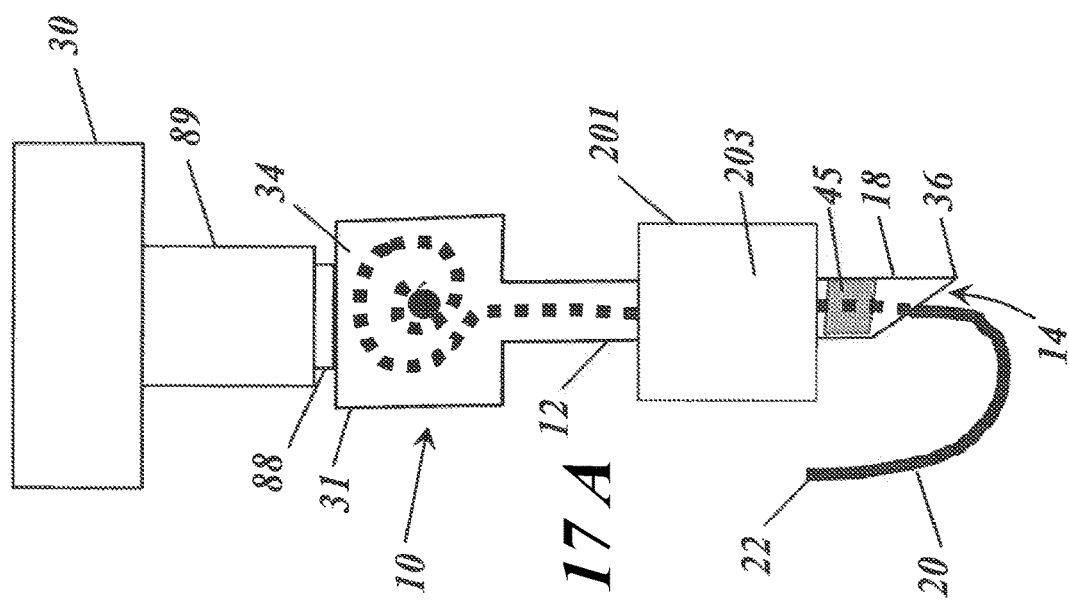

In an embodiment, as shown in FIGS. 17A and 17B, a driving mechanism 83 is positioned between and attached to a base 30 and the suturing device 10. A connecting mechanism 88 is optionally positioned between the suturing device 10 and the driving mechanism which allows the suturing device 10 to be removed after use and replaced by a new suturing device 10, thus allowing the driving mechanism 83 to be reused. The suturing device 10 may be any described herein. The connecting mechanism 88 may include a separate element to which both the driving mechanism 83 and the suturing device 10 can be connected, or it can be separate elements or features of the suturing device 10 and the driving mechanism 83 which connect to each other (examples of appropriate connections are threaded, friction, snap, and locking connections, all of which will be familiar with those skilled in the art). In an embodiment, the suturing device 10 is removably attached to the driving mechanism 83 and/or base 30.

The driving mechanism 83 is capable of applying a bi-directional force along the longitudinal axis of the hollow needle 12 of the suturing device 10 (the driving mechanism 83 may have an active driving mechanism to push the needle 12 forward towards its sharpened tip 36 and a spring for retracting the needle 12, or the driving mechanism may be capable of applying a force in either direction). The driving mechanism 83 comprises a drive element 89 and a movable element 85. The drive element 89 can be anything capable of producing movement of the movable element 85 appropriate to apply a force along the longitudinal axis of the hollow needle 12. While it will be obvious to those skilled in the field of drive mechanisms, examples of appropriate combinations of drive elements and movable elements are: a hydraulic or pneumatic drive mechanism which pushes or pulls on a piston-like or telescoping movable element; a rotary motor drive mechanism (e.g., an electrical rotary motor) turning a gear engaged with the helical threads of the drive element (e.g., a linear actuator); and an induction motor where the drive element is a stator and the movable element is the rotor (or vice versa).

In an embodiment, the driving mechanism 83 comprises a movable element 85 (e.g., a screw rod) capable of extending out from the drive element 89 (e.g., an electric rotary motor with gearing to turn the screw rod), and when the base is held relatively still (i.e., doesn't move much), as the movable element 85 extends out of the drive element 89 it pushes (or pulls) the needle 12, and hence its sharpened 36, directly away from (or directly towards) the base 30, preferably in a straight line parallel with the longitudinal axis of the lumen 14 of the hollow needle 12.

The movable element 85 is attached to the proximal end 16 (as shown in FIG. 1) of the suturing device 10 (the end opposite the sharpened tip 36 of the needle 12). If the sharpened tip 36 is against tissue, the movable element 85 will push the sharpened tip 36 of the needle 12 into the tissue a distance determined by the specifications of the driving mechanism (such as, for example, the linear distance the movable element of a linear actuator will travel when the linear actuator is actuated, or the length of travel of a pneumatically, electrically, mechanically or hydraulically driven, movable element, such as a piston). The driving mechanism is capable of applying a force in the opposite direction (i.e., towards the base 30) so that once the movable element 85 has attained its maximum extension or distance of travel, and the hollow needle 12 its maximum depth in the tissue, the driving mechanism is capable of reversing the direction of and retracting the movable element 85, and thereby pulling the needle 12 out of the tissue.

Actuation of the driving mechanism can be according to several schemes: in one, the operator must separately trigger outward (i.e., extension) and inward (i.e., retraction) movement of the movable element (e.g., such as by pressing separate buttons), with one trigger driving the needle 12 into the tissue and a separate trigger withdrawing the needle 12 from the tissue; in another, the operator triggers a single cycle of in and out simultaneously (such as by pressing a single button or pulling a single trigger) so that the needle is driven into the tissue and then automatically pulled out after reaching full depth as determined by the specifications or settings of the driving mechanism.

The suturing device 10 can be optionally disposed within the internal channel 203 of a guide block 201 such that movement of the suturing device 10 is constrained by the channel or rail 203 to travel along a fixed path. The guide block 201 may be attached to the base 30 so that it does not move relative to the base 30 or driving mechanism. In FIGS. 17A and 17B, the hollow needle 12 is within the internal channel 203 of a guide block 201 which is attached to the base 30 or to a common base, such as a laparoscopic instrument. The internal channel 203 has a cross-section of the same shape as the hollow needle 12, but slightly larger so that the hollow needle 12 may move freely within the internal channel 203, but only along its length. Having the guide block 201 is useful when the movable element is a hydraulically inflatable element or the inner cable of a Bowden cable. In another embodiment, the internal channel 203 conforms to the cross-sectional dimensions of the chamber (i.e., orthogonal to the direction of movement). In this embodiment, if a Bowden cable is being used, the outer sheathing of the cable may be attached directly to the guide block 201, or via an appropriate connector, and the inner cable may be attached directly to the suturing device 10 at the end opposite the sharpened tip 36 of the hollow needle 12.

In an embodiment, the maximum extension or length of travel of the movable element 85 is adjustable by the operator. In an embodiment, the base 30 is an instrument used in laparoscopic or arthroscopic surgeries, or adapted to be capable of attachment to such instruments. In an embodiment, the base 30 is an endoscope or adapted to be capable of attachment to an endoscope. In either of these embodiments, the motion of the hollow needle 12 when moved by the driving mechanism can be at any angle to the longitudinal axis of the endoscopic, laparoscopic or arthroscopic instrument, such as parallel, at a 15, 30, 45, 60, 75 or 90 degree angle, or at any angle in between.

In an embodiment, the base 30 is a grip adapted to be gripped by a hand, such as a pistol grip, or by one or more fingers and a thumb. In an embodiment, the driving mechanism 83 is attached to the base 30 by a hinging element 87 and the angle X of the movable element 85 relative to the base 30 is adjustable. In an embodiment, such angle X is adjustable via a manual or powered mechanism. In an embodiment, the base 30 is a flexible arm, such as, for example, a gooseneck arm. In an embodiment, the base 30 telescopes, such as parallel or orthogonal to the direction of travel of the movable element 85.

In an embodiment, movable element is a container constructed from an elastomeric material which can be inflated and deflated (hydraulically or pneumatically) to drive the hollow needle 12 along its longitudinal axis. In an embodiment, the force of the movable element in one direction is converted mechanically, hydraulically or pneumatically into a force in another direction, such as, for example, through a cam mechanism, a wedge, a gear, or tubing such that the hollow needle 12 and movable element do not move in the same direction. In an embodiment, the movable element is, or is attached to, the inner cable of a Bowden cable, which transmits mechanical force from the drive element to the hollow needle 12, directly or via additional linkages.

In an embodiment, there is a manual braking mechanism which allows a user to manually resist movement of the suture 20 through the lumen of the hollow needle of the suturing device. In an embodiment, there is a retraction mechanism which exerts tension on the suture 20 away from the sharpened tip 36 or distal end 18 of the hollow needle 12. The tension must be less than the amount necessary to overcome the self-retaining ability of the suture 20 in tissue.

Figure 11:
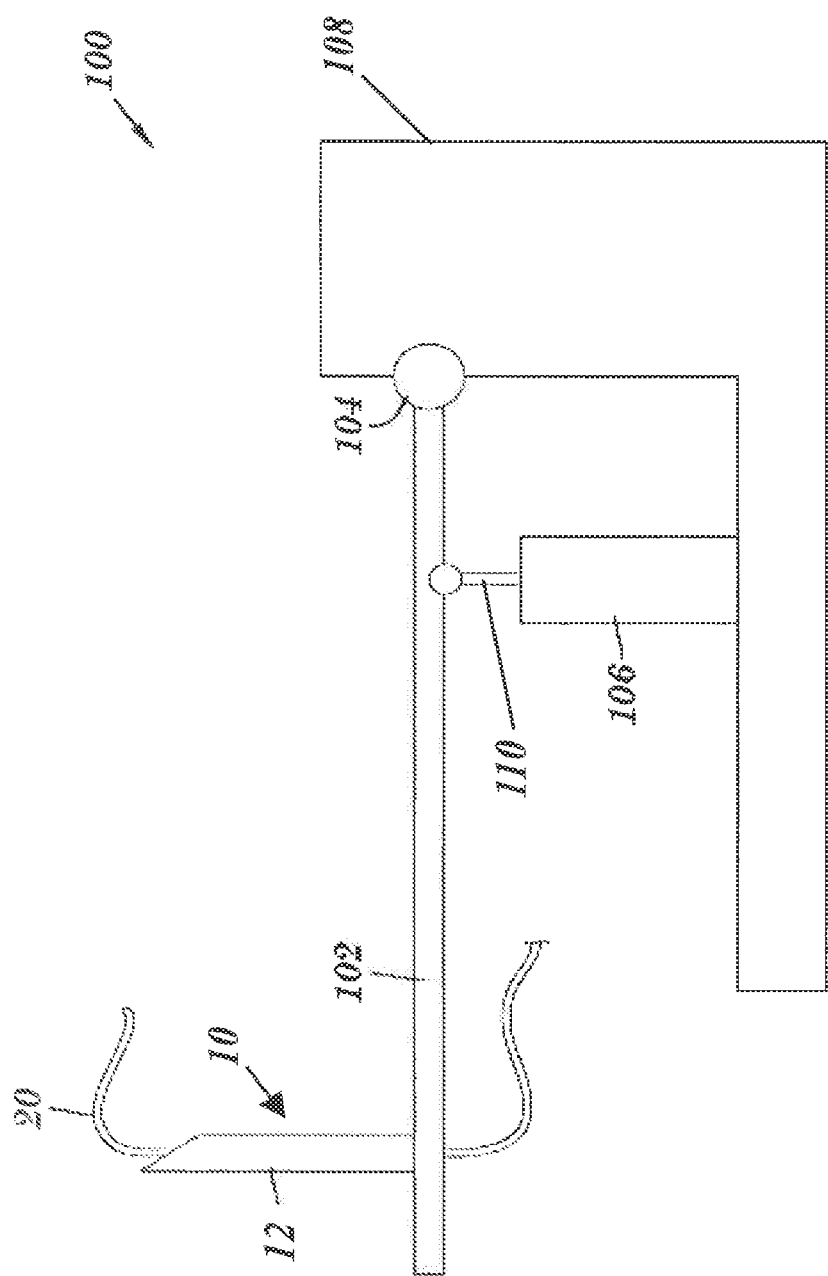
FIG. 11 is a schematic view of a mechanized suturing device including the suturing device shown in FIG. 1.

Referring now to FIG. 11, an aspect of the present invention is a mechanized suturing device 100 having the suturing device 10 including the hollow needle 12 affixed to an armature 102 at one end and the length self-retaining suture 20. The suture 20 is threaded into and through the lumen 14 of the hollow needle 12 within which the suture 20 can move (slide) relatively freely. The armature 102 is attached via a hinging element 104 to a mount 108.

The armature 102 is attached a movable element 110 (e.g., an arm or piston) to which a force can be applied by a driving element 106 to drive the armature, and thereby the needle 12, in the direction of the sharpened tip 36 (as shown in FIG. 1) at the distal end 18, or in the opposite direction. The energy required to cause the driving element 106 to move the movable element 110 can be provided electrically, pneumatically, hydraulically, manually, or mechanically. The depth to which the hollow needle 12 can be driven is optionally fixed or adjustable.

In this example, the portion of the suture 20 that is not in the lumen 14 of the hollow needle 12 or already used as sutures in tissue is optionally stored on a spool or in a chamber as shown in FIGS. 5 and 6, by way of example. Movement of the hinging element 104 may be manually controlled by the clinical operator or automatic, such as by detecting the distance the hollow needle 12 has moved from a previous hole and driving the hollow needle 12 into the tissue when that distance equals a predetermined amount. The mount 108 can be, by way of non-limiting examples, an instrument used in laparoscopic or arthroscopic surgeries, or capable of attachment to such instruments, an endoscope or capable of attachment to an endoscope, a grip adapted to be gripped by a hand, such as a pistol grip, or by one or more fingers and a thumb, or a gooseneck arm.

A further aspect of the present invention relates to a laparoscopic apparatus. The laparoscopic apparatus includes a shaft having a lumen extending between a distal end and a proximal end. A handle comprising a lever is connected is connected to the proximal end of the shaft. A rod or wire having a distal end and a proximal end is disposed within the lumen of the shaft. The proximal end of the rod or wire is connected to the lever of the handle. The apparatus further includes the suturing device of the present invention including a sharpened tip and a blunt proximal end. The suturing device is at least partially disposed within the lumen of the shaft at the distal end of the shaft and is connected at the blunt proximal end to the distal end of the rod or wire. Movement of the lever in a first direction pushes the sharpened tip of the needle out of the lumen of the shaft and movement of the lever in a second direction pulls the sharpened distal of the needle into the lumen of the shaft.

Referring now to FIGS. 18A and 18B, an apparatus 200 for laparoscopic or endoscopic deployment includes a handle 205, a shaft 207 that is hollow, having a proximal end 207*a* (relative to the user) connected to the handle 205 and a distal end 207*b* within which is situated the suturing device 10 (shown in FIG. 18A in the retracted position and in FIG. 18B in the extended position). The suturing device 10 has hollow needle 12 from the lumen 14 of which self-retaining suture 20 extends, the hollow needle 12 being connected at the proximal end 16 (as shown in FIG. 1 opposite the sharpened 36) to the distal end 31*a* of a chamber 31 in which a supply of the self-retaining suture 20 is disposed. An opening in the wall of the chamber 31 allows the suture 20 to pass from the chamber 31 into the lumen 14 of the hollow needle 12. A substantially rigid rod 209 is mounted within the lumen 212 of shaft 207, and is connected at its proximal end, directly or via a linkage, to lever 206 on handle 205 and at its distal end (away from the handle 205) to the suturing device 10. Alternatively, there may be no separate rod and the needle 12 itself provide the shaft. In this example, the needle 12 may be flexible, although a rigid needle could also be employed.

Referring again to FIGS. 18A and 18B, forward motion of lever 206, and thereby rod or wire 209, pushes the needle 12 out of the shaft 207. Backward motion of lever 206, and thereby of rod or wire 209, retracts needle 12 into shaft 207. Forward motion may be manual, such as by pulling an optional grip 206*a* incorporated into lever 206 towards the grip 205 *a* of the handle 205. Retraction of suturing device 10 may be manual or driven by a spring or elastic mechanism which stores energy as the needle 12 is being extended and releases the energy to retract the needle 12 back once the forward force is removed. Forward and backward motion of the rod or wire 209 can also be powered, such as pneumatically by gas from a carbon dioxide canister, electrically by an induction motor, hydraulically by a powered piston, or mechanically by a servo-motor or linear actuator, by way of examples only.

In an embodiment as shown in FIG. 18B, the suturing device 10 includes the hollow needle 12 having the sharpened tip 36 adapted for puncturing tissue and the proximal end 16 connected to chamber 31 in which a length of the self-retaining suture 20 is disposed, the suture 20 passing through an opening in the distal end 31*a* of the chamber 31 into the lumen 14 of the hollow needle 12 and passing out and extending beyond the sharpened distal tip 36.

In this example, the chamber 31 and hollow needle 12 are axially aligned, with the chamber 31 having a larger external dimension than needle 12. At the blunt proximal end 31*b*, the chamber 31 is connected to the rod or wire 209. Affixed within the distal end 207*b* of the shaft 207 is an annular guide 207*c* having an inner diameter slightly larger than the outer diameter of the needle 12 but smaller than the outer diameter of the distal end 31*a* of the chamber 31. A spring 221 is disposed within the lumen 212 of the shaft 207 between annular guide 207*c* and chamber 31, with the hollow needle 12 passing axially through the spring 221. The inner diameter of the spring 221 is larger than the outer diameter of the needle 12 and the inner diameter of the annular guide 207*c*, and the outer diameter of the spring 221 is less than the outer diameter of the distal end 31*a* of the chamber 31. When the needle 12 is extended by a forward force (away from the handle 205) on rod or wire 209, spring 221 is compressed between the distal end 31a of the chamber 31 and the annular guide 207c as suturing device 10 is pushed away from the handle 205, and when the forward force is removed, spring 221 pushes chamber 31 and thereby needle 12 and rod or wire 209 backwards towards handle 205. In FIGS. 18A and 18B, the suture 20 within the hollow needle 12 and chamber 31 is shown as a single dotted gray line, and the eternal contours of the portion of hollow needle 12 and chamber 31 inside shaft 207 are shown as dotted black lines.

In other embodiments, other types of spring mechanisms can be utilized to achieve automatic retraction of the needle 12 after its extension, such as by incorporating a spring-loaded grip 206a, or by attaching a spring or elastic mechanism to the lever appropriately. In an embodiment, both extension and retraction of the suturing device 10 are accomplished by manually moving lever 206 or grip 206a.

The laparoscopic embodiment can be adapted to a modular system, such as the Modular 3-Piece Laparoscopic Instruments sold by Millennium Surgical, where handle 205, shaft 207, and suturing device 10 can be disassembled by users for cleaning or for customizing the final apparatus 200 to the procedure, patient or surgeon. For instance, a suturing device using a larger diameter suture can be selected for certain operations and one with a finer suture can be selected for others. In an embodiment, rod or wire 209 is the suturing device 10, comprising a hollow needle 12 with or without a chamber 31 with self-retaining suture 20 disposed within the lumen 14 of the hollow needle 12, and the suturing device 10 is attached the blunt proximal end 31b to lever 206, either directly or through some short linkage.

Forward and/or backward motion may be powered, such as by a pneumatic, hydraulic, electromechanical or mechanical force applied to lever 206, optionally initiated by operating an optional trigger 205b (for example, depressing trigger 205b may release pressurized carbon dioxide from a canister or close a switch to provide electricity to a motor, linear actuator or induction motor). In one example, the shaft 207 optionally incorporates a flexible joint 220 at some point along its length between the distal end 207b and the proximal end 207a.

In an embodiment, the shaft 207 is bendable and/or flexible entirely or at multiple locations between the distal end 207b and the proximal end 207a. In one of such embodiments, shaft 207 is a Bowden Cable or gooseneck arm having a relatively stiff rod or wire 209 disposed within it. In an embodiment, shaft 207 is an endoscope having a lumen within which a relatively stiff rod or wire 209 is disposed. In embodiments with a flexible or bendable shaft 207, the rod or wire 209 is sufficiently flexible to be able to navigate changes in the shape of the shaft 207 (e.g., can flex with the shaft 207 as it is bent), and is stiff enough and/or mounted snuggly enough within the lumen 212 of shaft 207 that it will effectively transfer a force applied to lever 206 to suturing device 10 without kinking or otherwise failing.

In an embodiment, there is no rod or wire 209 and lumen 212 of shaft 207 is filled with hydraulic fluid between a piston, which is disposed within lumen 212 proximal to proximal end 207a of shaft 207 and connected to lever 206 (in one example, having a seal which prevents fluid from passing around the piston between it and the inner wall of shaft 207), and blunt proximal end 31b of the suturing device 10 (which is in this example similarly sealed to prevent the hydraulic fluid from passing around the distal end 18 of the suturing device 10); forward pressure on the lever 206 pushes the piston forward which pushes the hydraulic fluid towards distal end 207b of shaft 207, thereby also pushing suturing device 10 in the same direction and extending needle 12. Reversing the movement of the lever 206 pulls the piston and the suturing device 10 back.

In an embodiment, lever 206 is a planar push pad attached directly to the end of rod or wire 209, orthogonal to its longitudinal axis; the user presses down on lever 206 (i.e., the push pad) to extend needle 12 into tissue. In version of the preceding, handle 205 is a flange extending roughly orthogonal to shaft 207 at the proximal end 207a; the flange functions like the top collar of a syringe, and the lever like the push pad of a syringe plunger.

Apparatus 200 is operated by placing the distal end 207b of the shaft 207 at the position where a suture is to begin, and then extending the needle 12 out of shaft 207 into the tissue being sutured. After the needle 12 retracts or is retracted, the distal end 207b is relocated to the location of the next suture.

Another aspect of the present invention relates to a suturing kit including the suturing device of the present invention enclosed in packaging that maintains a sterile condition for the suturing device. The suturing kit further optionally includes a set of instructions An aspect of the present invention is a suturing kit containing the sterile hollow needle 12 and the length of sterile self-retaining suture 20 (e.g., barbed suture) enclosed in packaging that maintains their sterile condition. In an embodiment of the kit, a portion of the length of suture 20 is located within the lumen 14 of the hollow needle 12, with at least a portion of the suture 20 extending external to the lumen 14. An aspect of the invention is a kit for suturing containing any of the suturing devices described above. The kits optionally include a set of printed instructions describing a method for using the suturing device.

Another aspect of the present invention is a method of suturing tissue, such as using sutures to close a laceration or incision or to secure a graft that does not require that the needle fully pass through tissue. The method may be employed using any of the embodiments of suturing device 10 disclosed herein. The method has the steps of: (a) obtaining a length of the self-retaining suture 20 that has an outer diameter; (b) creating a puncture hole in tissue or tissues; and (c) inserting a portion of the suture 20 into the hole oriented such that the self-retaining aspect of the suture 20 (e.g., barbs 26) resists removal of the suture 20 from or its movement out of the hole. In one embodiment, steps (b) and (c) are repeated one or more times at separate locations in the tissue or tissues until suturing is complete, resulting in a series of holes in the tissue or tissues into which a portion of the suture 20 has been inserted and embedded connected by lengths of suture 20 external to the tissue, excepting the first hole and the last hole. In another embodiment, there is a step (d) of cutting the suture 20. In a further embodiment, the holes are created proximal to a laceration, cut, incision or wound. In another embodiment, there are two tissues, a graft and the tissue which is being grafted, and each hole penetrates both tissues. In an embodiment, two tissues are being sutured together, such as in anastomisis of lumens such as blood vessels.

In an embodiment, the hole in the tissue is created by a substantially rigid rod. For the purposes of this embodiment, a substantially rigid rod is one on which an axial force can be applied that is sufficient to pierce the tissue and create a hole. In an embodiment, the substantially rigid rod has a sharp end (e.g., a needle). In an embodiment, the suture 20 has a leading end 22 that is sharp. In an embodiment, the rod has a lumen (i.e., the rod is a tube) having an internal diameter larger than the outer diameter of the suture.

In an embodiment, inserting a portion of the suture 20 into the hole is accomplished by pushing a substantially rigid rod into the tissue. For the purposes of this embodiment, a substantially rigid rod is one on which an axial force can be applied that is sufficient for inserting the portion of suture 20 into the hole.

An aspect of the present invention is a method of suturing that has the steps of: (a) obtaining the hollow needle 12 having a proximal end 16 and a sharpened tip 36 located at the distal end 18, the lumen 14 of the hollow needle 12 having an inner diameter; (b) obtaining the length of self-retaining suture 20 that has an outer diameter smaller than the inner diameter of the lumen 14 of the hollow needle 12, the suture 20 having leading end 22 and trailing end 24; (c) threading the leading end 22 of the suture 20 into the lumen 14 of the hollow needle 12 until a portion of the leading end 22 of the suture 20 extends beyond the sharpened tip 36 located at the distal end 18 of the hollow needle 12 and the trailing end 24 of the suture 20 is within the lumen 14 or extends beyond the proximal end 16 of the hollow needle, with the self-retaining element or elements of the suture (e.g., barbs 26) oriented such that if the lumen 14 were a hole in tissue, the 26 would resist movement away from the distal end 18 of the hollow needle 12; (d) pushing the hollow needle 12 and a portion of the suture 20 into a tissue or tissues, creating a hole in the tissue or tissues; and (e) pulling the hollow needle 12 out of the tissue or tissues without withdrawing the portion of the suture 20 from the hole in the tissue. In an embodiment, steps (d) and (e) are repeated one or more times at separate locations in the tissue or tissues until suturing is complete, resulting in a series of holes in the tissue or tissues into which a portion of the suture 20 has been inserted and embedded connected by lengths of the suture 20, excepting the first hole and the last hole. In an embodiment, there is a step (0 of cutting the suture 20.

An aspect of the present invention is a method of suturing that has the steps of: (a) obtaining a hollow needle 12, which has a proximal end 16, a distal end 18, and a lumen 14 having an inner diameter, into which a length of self-retaining suture 20, which has a leading end 22, a trailing end 24, and an outer diameter smaller than the inner diameter of the lumen 14 of the hollow needle 12, has been threaded until a portion of the leading end 22 of the suture 20 extends beyond the distal end 18 and the trailing end 24 of the suture 20 is within the lumen 14 of the hollow needle 12 or extends beyond the proximal end 16 of the hollow needle 12, said suture 20 oriented within the lumen 14 such that the self-retaining element or elements of the suture 20 (e.g., barbs 26) would, if the lumen 14 were a hole in tissue, resist movement of the suture 20 within the lumen 14 toward the proximal end 16 of the hollow needle 12; (b) pushing the hollow needle 12 and a portion of the suture 20 into a tissue or tissues, creating a hole in the tissue or tissues; and (c) pulling the hollow needle 12 out of the tissue or tissues without fully withdrawing the portion of suture 20 from the tissue or tissues. In an embodiment, steps (b) and (c) are repeated one or more times at separate locations in the tissue or tissues until suturing is complete, resulting in a series of holes in the tissue or tissues into which a portion of the suture 20 has been inserted and embedded connected by lengths of suture 20, excepting the first hole and the last hole. In an embodiment, there is a step (d) of cutting the suture 20.

In an embodiment, a portion of the trailing end of the suture 20 is wound around a spool or gathered in bundle and plays during suturing.

Having thus described the basic concept of the invention, it will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A suturing device comprising:
a hollow needle having a length extending between a proximal end and a distal end and defining a lumen having an inner diameter;
a length of surgical suture having a leading end and a trailing end and sized to fit within the inner diameter of the lumen, at least a portion of the surgical suture being located within the lumen of the hollow needle; and
a base element coupled to the proximal end of the hollow needle by a gimbaled or hinged coupling.

2. The suturing device of claim 1, wherein a first portion of the leading end of the length of surgical suture extends beyond the distal end of the lumen or a second portion of the trailing end of the length of the surgical suture extends beyond the proximal end of the lumen.

3. The suturing device of claim 1, wherein the distal end of the hollow needle has at least one sharpened edge configured to penetrate a tissue.

4. The suturing device of claim 1, wherein the surgical suture is a unidirectional self-retaining suture comprising one or more barb structures located along the length of the surgical suture configured to engage a tissue when inserted therein to resist movement out of contact with the tissue.

5. The suturing device of claim 1, wherein the hollow needle has one or more radii of curvature along its length.

6. The suturing device of claim 1, wherein the hollow needle has a longitudinal axis extending between the proximal and distal ends and has a bent portion, that is bent at an angle of ate at least 45 degrees with respect to the longitudinal axis of the hollow needle, proximate to the distal end that is bent with respect to the longitudinal axis of the hollow needle.

7. The suturing device of claim 1, wherein the base element has and further comprises a spooling element located within the inner chamber configured to hold at least a portion of the length of the surgical suture, and wherein the base element further comprises a spooling element located within the inner chamber to hold at least a portion of the length of the surgical suture.

8. The suturing device of claim 1, further comprising a spooling element coupled to the hollow needle proximate the proximal end to hold at least a portion of the length of surgical suture.

9. The suturing device of claim 1, further comprising a cutting element coupled to the hollow needle proximate the distal end.

10. The suturing device of claim 1, wherein the hollow needle further comprises a second lumen configured to be coupled to a syringe or bulb for delivery of one or more viscous or liquid materials to the distal end of the hollow needle.

11. The suturing device of claim 1 further comprising:
a movable element supported by a base and affixed to the hollow needle; a drive element coupled to the movable element, wherein said drive element is configured to be capable of moving the movable element relative to the base to push the distal end of the hollow needle toward and into tissue in use and pull the distal end of the hollow needle away from and out of the tissue, wherein the drive element is one of a manual, mechanical, electrical, hydraulic, or pneumatic drive element.

12. A laparoscopic apparatus comprising:
a shaft having a lumen extending between a distal end and a proximal end;
a handle comprising a lever, wherein the handle is connected to the proximal end of the shaft;
a rod or wire having a distal end and a proximal end disposed within the lumen of the shaft, the proximal end of the rod or wire being connected to the lever of the handle; and
a suturing device at least partially disposed within the lumen of the shaft, the suturing device of claim 1 including:
a hollow needle having a length extending between a proximal end and a distal end and defining a lumen having an inner diameter;
a length of surgical suture having a leading end and a trailing end and sized to fit within the inner diameter of the lumen, at least a portion of the surgical suture being located within the lumen of the hollow needle; and
a base element coupled to the proximal end of the hollow needle by a gimbaled or hinged coupling, further comprising a sharpened distal tip and a blunt proximal end, wherein the suturing device is at least partially disposed within the lumen of the shaft at the distal end of the shaft, the suturing device connected at the blunt proximal end to the distal end of the rod or wire, wherein movement of the lever in a first direction pushes the sharpened distal tip of the needle out of the lumen of the shaft and movement of the lever in a second direction pulls the sharpened distal of the needle into the lumen of the shaft.

13. The laparoscopic apparatus of claim 12, further comprising a spring that provides a force to pull the distal tip of the needle into the lumen of the shaft after the distal tip of the needle has been extended by applying an appropriate force to the lever.

14. The laparoscopic apparatus of claim 12, wherein the rod or wire is flexible.

15. The laparoscopic apparatus of claim 12, wherein the suturing device acts as the rod or wire.

16. The laparoscopic apparatus of claim 12, wherein the suturing device further includes a sharpened tip and a blunt proximal end, wherein the suturing device is at least partially disposed within the lumen of the shaft at the distal end of the shaft, the suturing device connected at the blunt proximal end to the distal end of the rod or wire, wherein movement of the lever in a first direction pushes the sharpened tip of the needle out of the lumen of the shaft and movement of the lever in a second direction pulls the sharpened distal of the needle into the lumen of the shaft.

17. The suturing device of claim 1, further comprising an armature having a first end attached to a movable element, and a second end attached to the base element of the suturing device.

18. The suturing device of claim 1, wherein the base element is connected to a mechanical system comprising:
a hinging element;
an armature including:
a first end connected to the hinging element, and
a second end attached to the base element of the suturing device;
a driving element; and
a movable element connected to the driving element and the armature.

19. The suturing device of claim 1, further comprising:
a driving mechanism including
a drive element,
a movable element connected to the drive element, and
a connecting mechanism coupled to the movable element of the driving mechanism.

20. The suturing device of claim 19, further comprising a guide block having an internal channel receiving the needle.

* * * * *